(12) United States Patent
Pullabhatla et al.

(10) Patent No.: US 11,574,719 B2
(45) Date of Patent: Feb. 7, 2023

(54) SYSTEMS, METHODS, AND STRUCTURES FOR MEDICATION ADHERENCE

(71) Applicant: QuantaEd, LLC, San Diego, CA (US)

(72) Inventors: Ashwini Pullabhatla, San Diego, CA (US); Mehran Mehregany, San Diego, CA (US)

(73) Assignee: Quanta Ed, LLC, San Diego, CA (US)

( * ) Notice: Subject to any disclaimer, the term of this patent is extended or adjusted under 35 U.S.C. 154(b) by 263 days.

(21) Appl. No.: 16/610,807

(22) PCT Filed: May 7, 2018

(86) PCT No.: PCT/US2018/031415
§ 371 (c)(1),
(2) Date: Nov. 4, 2019

(87) PCT Pub. No.: WO2018/204921
PCT Pub. Date: Nov. 8, 2018

(65) Prior Publication Data
US 2020/0066387 A1 Feb. 27, 2020

Related U.S. Application Data

(60) Provisional application No. 62/501,982, filed on May 5, 2017.

(51) Int. Cl.
G16H 20/10 (2018.01)
G16H 10/60 (2018.01)
G16H 70/40 (2018.01)
G06N 20/00 (2019.01)
G06N 5/04 (2006.01)

(52) U.S. Cl.
CPC ............. *G16H 20/10* (2018.01); *G16H 10/60* (2018.01); *G16H 70/40* (2018.01); *G06N 5/045* (2013.01); *G06N 20/00* (2019.01)

(58) Field of Classification Search
CPC ........ G16H 20/10; G16H 40/63; G16H 10/60; G16H 70/40
USPC .......................................................... 705/2
See application file for complete search history.

(56) References Cited

U.S. PATENT DOCUMENTS

2005/0267356 A1* 12/2005 Ramasubramanian ... A61J 1/03
600/411
2007/0016443 A1 1/2007 Wachman et al.
2012/0025999 A1* 2/2012 Needham ............... G16H 40/67
340/686.6
2013/0117696 A1 5/2013 Robertson et al.
(Continued)

FOREIGN PATENT DOCUMENTS

WO WO-2017139761 A1 * 8/2017 ........ A61M 5/14244

OTHER PUBLICATIONS

Lindsey Dayer; Smartphone medication adherence apps: Potential benefits to patients and providers; https://www.sciencedirect.com/journal/journal-of-the-american-pharmacists-association/vol/53/issue/2; Mar.-Apr. 2013, pp. 172-181 (Year: 2013).*
(Continued)

Primary Examiner — Hiep V Nguyen
(74) Attorney, Agent, or Firm — Kaplan Breyer Schwarz, LLP

(57) ABSTRACT

Aspects of the present disclosure describe systems, methods, and structures for patient medication adherence.

20 Claims, 22 Drawing Sheets

(56) References Cited

U.S. PATENT DOCUMENTS

| | | | |
|---|---|---|---|
| 2013/0222135 A1* | 8/2013 | Stein | A61J 7/0481 340/540 |
| 2014/0277702 A1* | 9/2014 | Shaw | G07F 17/0092 700/232 |
| 2015/0048102 A1* | 2/2015 | Dickie | A61J 7/0436 221/2 |

OTHER PUBLICATIONS

"The Future of Medication Adherence", "McKesson Patient Relation Solutions", Mar. 1, 2012, Publisher: McKesson Corporation, 8 pp.

Authorized Officer: Lee W. Young, International Search Report and Written Opinion issued in PCT application No. PCT/US2018/031415, dated Aug. 9, 2018, 12 pp.

Director: Thomas Forissier, et al., "Patient Adherence: The Next Frontier in Patient Care", "Vision & Reality", Publisher: Capgemini Consulting, dated 2011, 44 pp., 9th Edition.

Mehran Mehregany, PhD, "Wireless Health: Remaking of Medicine by Pervasive Technologies", Nov. 30, 2014, Publisher: AuthorHouse, ISBN-13: 9781496934147, Chapter 16.

Nagaraja Srivatsan et al., "Medication Adherence in the Real World", "Cognizant 20-20 Insights", Oct. 1, 2014, Publisher: Cognizant, 13 pp.

Niteesh K. Choudhry MD, PhD et al., "Effect of Reminder Devices on Medication Adherence—The REMIND Randomized Clinical Trial", "JAMA Internal Medicine", Feb. 27, 2017, Publisher: American Medical Association, doi:10.1001/jamainternmed.2016.9627, pp. 624-631, vol. 177, No. 5.

* cited by examiner

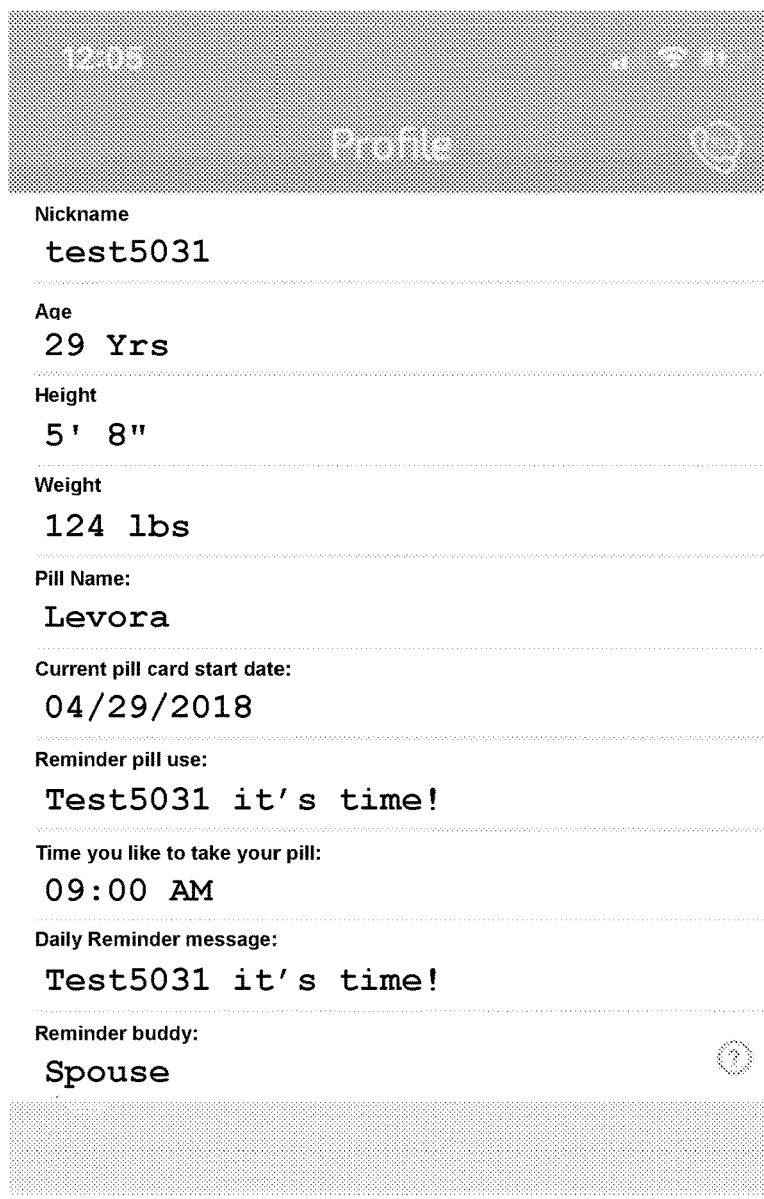
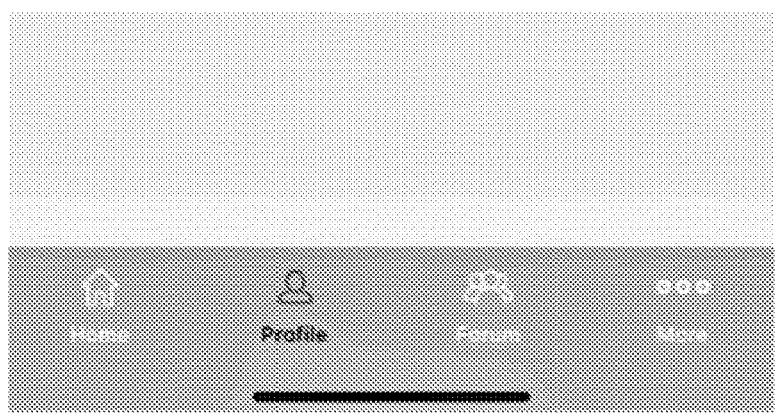
FIG. 4

| Terminology | Adherence |

Lets share some terminology Before moving ahead

"OCP" means oral contraceptive pill, often called the pill.

"Adherence" means the extent to which we follow the prescribed dose and timing of a medication as prescribed "Perfect adherence" means we are always taking the right dose at the right time.

"Typical adherence" means the average adherence amount and accounts for missed and mistimed pills, limited understanding of instructions and/or lapses in use.

Next

*FIG. 5(A)*

| Terminology | Adherence |
|---|---|

Lets share some terminology Before moving ahead

Studies show that:

* Women who practice perfect adherence over the first year of use only have 0.3% incidence of unintended pregnancy. The same risk increases to 9% with typical adherence!

* A lot of us don't realize that missing just one pill places us at increased risk of pregnancy.

* Over 40% of us admit to missing one or more pills in any given 3-month period.

In short, the more pills we miss, the higher our chance of unintended pregnancy.

Continue to LOGIN page

*FIG. 5(B)*

1. What time do you take your pill?

12:06 PM

Tell us about your adherence history

2. I forget to take my pill.
- ● Always
- ○ Often
- ○ Less than often
- ○ Rarely
- ○ Never 3. I alter the dose of my pill.
- ● Always
- ○ Often
- ○ Less than often
- ○ Rarely
- ○ Never 4. I stop taking my pill for a while when I am not supposed to.
- ● Always
- ○ Often
- ○ Less than often
- ○ Rarely
- ○ Never 5. I decide to miss out a dose of my pill.
- ● Always
- ○ Often
- ○ Less than often
- ○ Rarely
- ○ Never

| Cancel | Next |

*FIG. 7(A)*

○ Never

3. I alter the dose of my pill.
◉ Always  ○ Often
○ Less than often  ○ Rarely
○ Never 4. I stop taking my pill for a while when I am not supposed to.
◉ Always  ○ Often
○ Less than often  ○ Rarely
○ Never 5. I decide to miss out a dose of my pill.
◉ Always  ○ Often
○ Less than often  ○ Rarely
○ Never 6. I take less than instructed.
◉ Always  ○ Often
○ Less than often  ○ Rarely
○ Never 7. Do you take the Reminder pills?

| Cancel | Next |

*FIG. 7(B)*

SYSTEMS, METHODS, AND STRUCTURES FOR MEDICATION ADHERENCE

CROSS REFERENCE TO RELATED APPLICATIONS

This application claims the benefit of U.S. Provisional Patent Application Ser. No. 62/501,982 filed 5 May 2017 the entire contents of which are incorporated by reference as if set forth at length herein.

TECHNICAL FIELD

This disclosure relates to systems, methods, and structures that facilitate adherence to a medication regimen by a patient.

BACKGROUND

As is known, adherence to a medication regimen—and particularly to a prescribed medication regimen—is an essential and critically important element to regimen efficacy and a desired therapeutic outcome.

Given this importance, systems, methods, and structures that facilitate adherence to a medication regimen would represent a welcome addition to the art.

SUMMARY

An advance in the art is made according to aspects of the present disclosure directed to systems, methods, and structures that facilitate adherence to a medication regimen—and in particular to a prescription medication regimen. In sharp contrast to the prior art, systems, methods, and structures according to the present disclosure advantageously employ the patients social circle to promote adherence. In illustrative embodiments, systems, methods and structures according to the present disclosure will send notification(s) to one or more patient "reminder buddie" when it is determined that patient adherence to the medication regime is not sufficiently compliant. In this inventive manner—and in sharp contrast to the prior art—systems, methods, and structures according to the present disclosure provide greater patient adherence to such medication regimes.

BRIEF DESCRIPTION OF THE DRAWING

A more complete understanding of the present disclosure may be realized by reference to the accompanying drawing in which:

FIG. 4 shows an illustrative profile screen according to aspects of the present disclosure; and FIG. 5(A) and FIG. 5(B) are illustrative application screens about: FIG. 5(A) adherence; and FIG. 5(B) the importance of adherence; —both according to aspects of the present disclosure;

FIG. 6(A) reference information; and FIG. 6(B) OCP library; —both according to aspects of the present disclosure;

FIG. 7(A), FIG. 7(B) and FIG. 7(C) are illustrative application screens for: FIG. 7(A), FIG. 7(B) addressing past OCP adherence during onboarding; and FIG. 7(C) help for anticipated reference data; —both according to aspects of the present disclosure;

Figure 1:
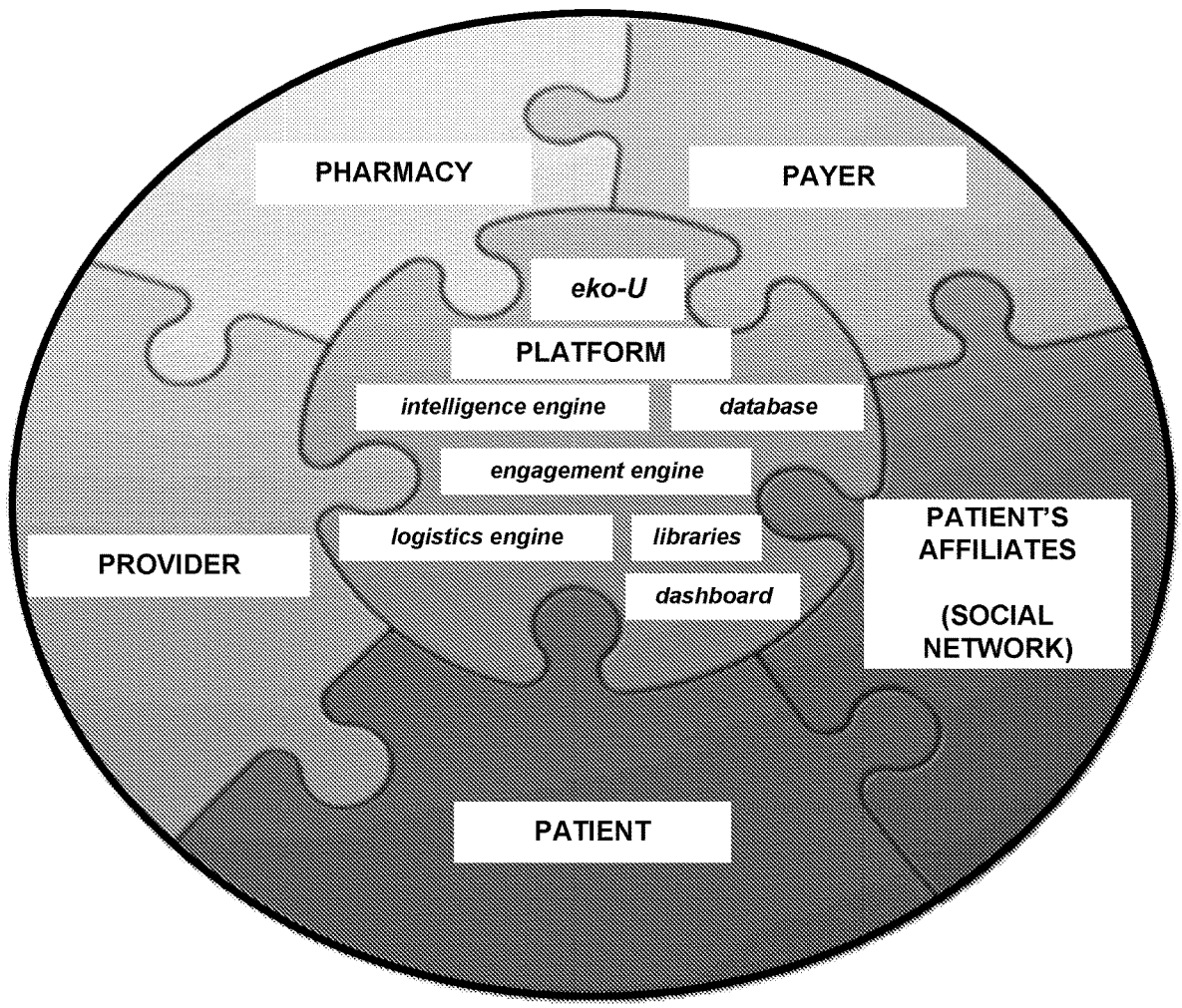
FIG. 1 is a schematic diagram depicting illustrative components of an adherence architecture according to aspects of the present disclosure.

The illustrative embodiments are described more fully by the Figures and detailed description. Embodiments according to this disclosure may, however, be embodied in various forms and are not limited to specific or illustrative embodiments described in the drawing and detailed description.

DESCRIPTION

The following merely illustrates the principles of the disclosure. It will thus be appreciated that those skilled in the art will be able to devise various arrangements which, although not explicitly described or shown herein, embody the principles of the disclosure and are included within its spirit and scope.

Furthermore, all examples and conditional language recited herein are intended to be only for pedagogical purposes to aid the reader in understanding the principles of the disclosure and the concepts contributed by the inventor(s) to furthering the art and are to be construed as being without limitation to such specifically recited examples and conditions.

Moreover, all statements herein reciting principles, aspects, and embodiments of the disclosure, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

Thus, for example, it will be appreciated by those skilled in the art that any block diagrams herein represent conceptual views of illustrative circuitry embodying the principles of the disclosure.

In addition, it will be appreciated by those skilled in art that any flow charts, flow diagrams, state transition diagrams, pseudocode, and the like represent various processes which may be substantially represented in computer readable medium and so executed by a computer or processor, whether or not such computer or processor is explicitly shown.

Unless otherwise explicitly specified herein, the FIGS. comprising the drawing are not drawn to scale.

Finally, as used in this disclosure, the use of the word "pill" is intended to include a wide range of medication forms, including a pill, capsule, lozenge, and the like. The use of the word "medication" is intended to include the wider range of therapy drug forms, including pills, oral strips, syrups, and the like.

By way of illustrative example only, we note that this disclosure is presented illustratively using a prescription oral contraception regimen for illustrative and discussion purposes only. Those skilled in the art will readily appreciate and understand that the principles, methods, structures, and systems according to the present disclosure will apply equally well to any administered medication, whether by patent or others and whether such medication is prescription or other.

As will be readily known and appreciated, patient adherence to an oral contraceptive pill (OCP) regimen is of the utmost importance to the well-being and desired therapeutic outcome(s) for that patent. Due to its importance and relative complexity, this OCP regimen is used here as an illustrative example to elucidate the concepts herein. The rationale for considering OCP adherence as an example is its relative complexity, e.g., missing just one pill increases risk of pregnancy and missed pills can be made up by taking manufacturer-specified remedial steps over appropriate time windows. Those skilled in the art will readily appreciate and understand that the concepts disclosed herein are broadly applicable to various medications and therapies, in which adherence guidelines are usually simpler.

As is well known in the medical arts, an OCP regimen works very well when administered with perfect adherence (i.e., when always taking the right pill at the right time). Unfortunately, over 40% of women admit to missing one or more pills in any given 3-month period. In fact, Great Britain's largest manufacturer of OCP—Schering Health Care Ltd—reports that on average women forget to take their pill eight times a year. And while most of these women do know they must take remedial steps when a pill is missed, few know what those remedial steps are. Furthermore, only 10% know missing just one pill places them at risk of pregnancy.

It is notable that with respect to reminders and low-cost reminder devices, a major study funded by CVS Health and published Feb. 17, 2017 entitled "Effect of Reminder Devices on Medication Adherence: The REMIND Randomized Clinical Trial" in *JAMA Internal Medicine* concluded:

"In a large, pragmatic, comparative-effectiveness randomized clinical trial of patients across a broad range of chronic conditions, low-cost [reminder] devices did not measurably improve medication adherence. Future research should focus on effective strategies to ensure uptake and sustained use of these interventions."

In other words, simply reminding a patient is not effective in improving adherence.

Patient adherence is advantageously improved by systems, methods, and structures according to aspects of the present disclosure which advantageously facilitates the automated management of a medication regime thereby driving patient adherence. Such systems according to aspects of the present disclosure employ an expert system constructed around a patient-centric adherence model—referred to herein as "eko-U".

Turning now to FIG. 1, there is shown is a schematic diagram depicting illustrative components of an adherence architecture (eko-U) according to aspects of the present disclosure. As may be observed from that diagram illustratively shown in the figure, elements involved in patient medication regime adherence may generally include—in no specific order of importance—1) a patient; 2) a provider of medical care—i.e., doctors, nurses, other care givers, etc., 3) a pharmacy from which medication is dispensed; 4) a payer—i.e., third-party payer (insurance company); and—of particular importance to the present disclosure—4) the patient's affiliates including her social network and/or family, and/or friends, and/or advocates, and/or other designated persons with whom the patient has some relationship (also referred to as "reminder buddy" herein). One aspect of the present disclosure is the novel observation that a patient's affiliates are better positioned relative to the patient as compared to others (i.e., doctors, nurses, pharmacist, insurance companies, etc.) because of their—perhaps personal—bond or other relationship with that patient. In addition, a patient's affiliates may be affected by a patients' non-adherence—thereby providing additional motivation to them to facilitate patient compliance/adherence to a medication regime. Finally, patient affiliates are generally volunteers, i.e., they do not cost the other "care circle" components as shown in the figure. It should be noted that the reminder buddy feature may also be implemented by artificial intelligence technology and alike—thereby being a machine persona that communicates like a human via phone call, e-mail, texting, etc.

Illustratively shown in FIG. 1—in addition to the architectural elements described above, are the components of the eko-U platform that integrates the architectural elements namely, an intelligence engine, an engagement engine, a logistics engine, a database, a set of libraries, and a dashboard. Further aspects of these specific eko-U platform components will be described operationally in more detail throughout this disclosure.

As we shall show and describe, systems, methods, and structures according to aspects of the present advantageously drive teaching, motivating, and enabling and further patient engagement by implementing these architectural elements. As will become readily apparent to those skilled in the art, illustrative eko-U implementation according to further aspects of the present disclosure employs: (i) integrating and automating the medication management circle; (ii) collecting and analyzing data in real time from connected smart devices, electronic databases (e.g., EMRs, EHRs, etc.), and direct entry; and (iii) engaging the patient—and providing options for engagement of other—in the medication management circle, collectively referred to hereafter as 'people'.

By way of a quite simple, illustrative example, let us assume that a patient visits a doctor who then prescribes medication and regimen. As a result of that visit/prescription, eko-U forwards medication data (e.g., from authoritative source or direct entry) to a pharmacy, which in-turn notifies the patient when the prescription is ready.

Adherence to the regimen is advantageously monitored using connected smart devices/instruments—or direct patient entry—and supported through engagement of the relevant people in the medication management circle. Exemplary, non-limiting descriptions of adherence-monitoring devices/instruments and methods are provided in U.S. patent application Ser. No. 15/223,779 and U.S. patent application Ser. No. 15/170,121, each of which is incorporated herein by reference.

In the simple illustrative example described herein, episodic adherence status may be provided by such instruments, or by other means, to the patient's affiliates for support. Periodic adherence assessment(s) may be provided to the doctor/doctor's office automatically or on demand, as well as the scheduling of remedial appointments (including automatically based on prescribed adherence criteria). These adherence assessments may also be made available to payers and pharmacies automatically or on demand as specifically authorized by the patient. Refills and follow up appointments may likewise be automatically scheduled.

We note that eko-U is constructed with mobility in mind, using state-of-the-art technologies in sensing, communication, computing and social networking. Its architecture and implementation(s) may advantageously employ cloud computing or other networked computing environments. It advantageously allows patients to selectively provide—or deny—access to various functionalities and data through permission settings.

The expert system component of eko-U comprises several components:

1. The intelligence engine provides decision support and—as such—is the "brain" of the system. Its implementation may include artificial intelligence, machine learning, deep learning and/or data science provides the following operational capabilities:
    a. Understanding the prescribed medication regimen
    b. Analyzing the patient's adherence to the prescribed medication regimen, both quasi-static and dynamic, using patient-entered adherence data and/or adherence-tracking smart devices (e.g., pill cases, bottles, etc.), such as those described in U.S. patent application Ser. Nos. 15/223,779 and 15/170,121.
    c. Analyzing and classifying any gap(s) between Items 1.a and 1.b
    d. Anticipating logistical adherence challenges by
        i. Analyzing the patient's calendar
        ii. Analyzing the relative distance between the adherence-tracking smart devices (i.e., the medicine) and the patient
        iii. Analyzing Items 1.d.i and 1.d.2 in correlation with traffic pattern along the relative distance
    e. Analyzing side effects and (when applicable) correlating them to data from other health and wellness applications on the patient's smart phone
    f. Analyzing and prioritizing people participation needs in the care circle
    g. Anticipating refill and appointment requirements
    h. Analyzing, synthesizing, and visualizing data
    i. Analyzing engagement efficacy of engagement strategies
    j. Analyzing shopping behavior and preferences 2. The logistics engine handles operational coordination among the people, entities, and medication supplies. Its implementation realizes the following key capabilities:
    a. Analyzing and synthesizing tasks, task breakdowns, and task participants using results from Item 1
    b. Scheduling and executing actions related to Item 2.a
    c. Generating timely reminders, alerts, notifications, messages, and the like in support of Item 2b
    d. Tracking the outcomes of Item 2.b
    e. Following up and closing delinquent outcomes 3. A separate engine handles engagement of the stakeholders. Its implementation realizes the following key capabilities:
    a. Choosing custom engagement strategies for driving patient adherence (both quasi-static and dynamic) based on results from Item 1
    b. Choosing custom engagement strategies in support of Item 2.e
    c. Choosing custom reminders, alerts, notifications, messages, and the like (based on results from Items 3.a and 3.b) to drive intended outcomes 4. A database aggregates all captured data. eko-U incorporates data translators to allow data capture from different/others' devices and databases. It works seamlessly with eko-U's adherence-tracking devices and disease-specific apps.

5. A dashboard provides tools for data analysis, synthesis, and visualization for adherence, efficacy, side effects and safety for individual and population health.

6. The libraries are repositories of medication reference data. Tools support authoring custom medication libraries, for example for clinical studies.

User Interfaces

With additional reference to FIG. 1, we note that interface(s) for the various users of eko-U are tailored to their access device(s). In describing such devices, we note that those described herein are only illustrative and not limiting.

Figure 2:
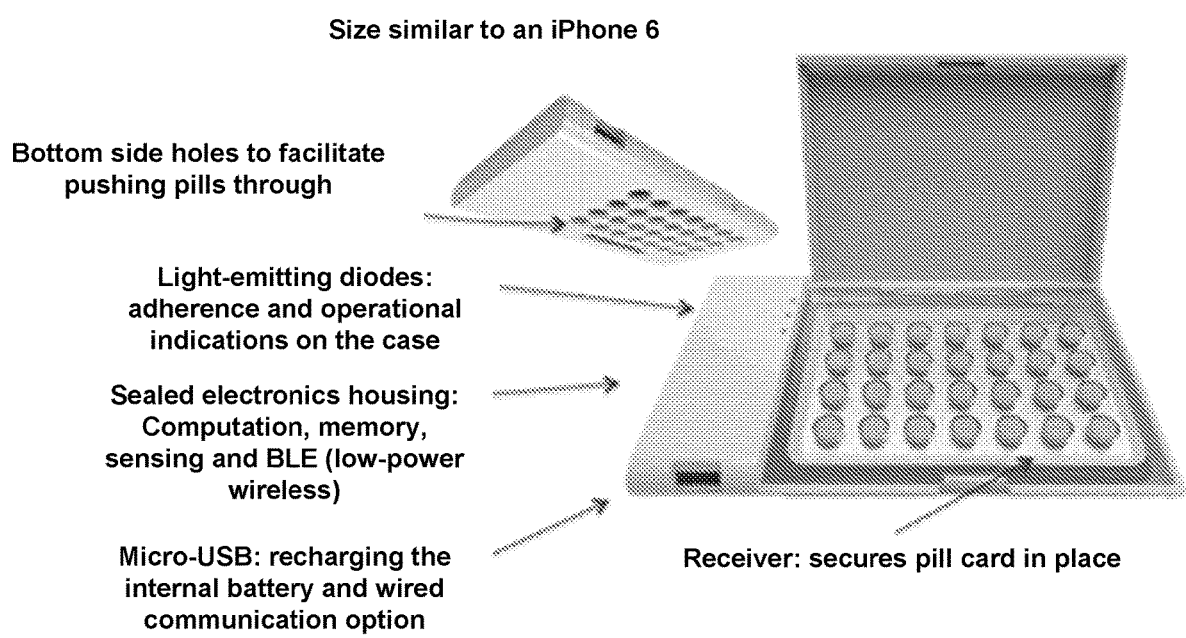
FIG. 2 is a schematic diagram of an illustrative reusable smart-pill case for OCP patients according to aspects of the present disclosure.

Patient—A patient may advantageously use a mobile device (e.g., smart phone, tablet, Watch, or another smart/intelligent device, etc.). Such smart devices are accessible to patients and connected (wired and/or wirelessly) to mobile devices to enable monitoring of patients' medication regime adherence. Examples of such smart devices for supporting OCP adherence were described in U.S. patent application Ser. No. 15/223,779, filed Jul. 29, 2016. FIG. 2 illustrates one such smart device example.

Patient's Affiliates—The patient affiliates also typically use mobile devices.

Provider—The healthcare provider (i.e., typically a doctor, physician assistant, nurse, etc.) typically uses a work desktop device, though the use of employer-provided and personal mobile devices is not uncommon.

Pharmacy—The user interface of the pharmacy personnel is typically a work desktop device.

Payer—The user interface of staff of the health insurer is typically a work desktop device.

In an illustrative embodiment, mobile devices run mobile application software, including ones related to eko-U. Desktop devices would use a Web-based interface to eko-U.

Figure 3:
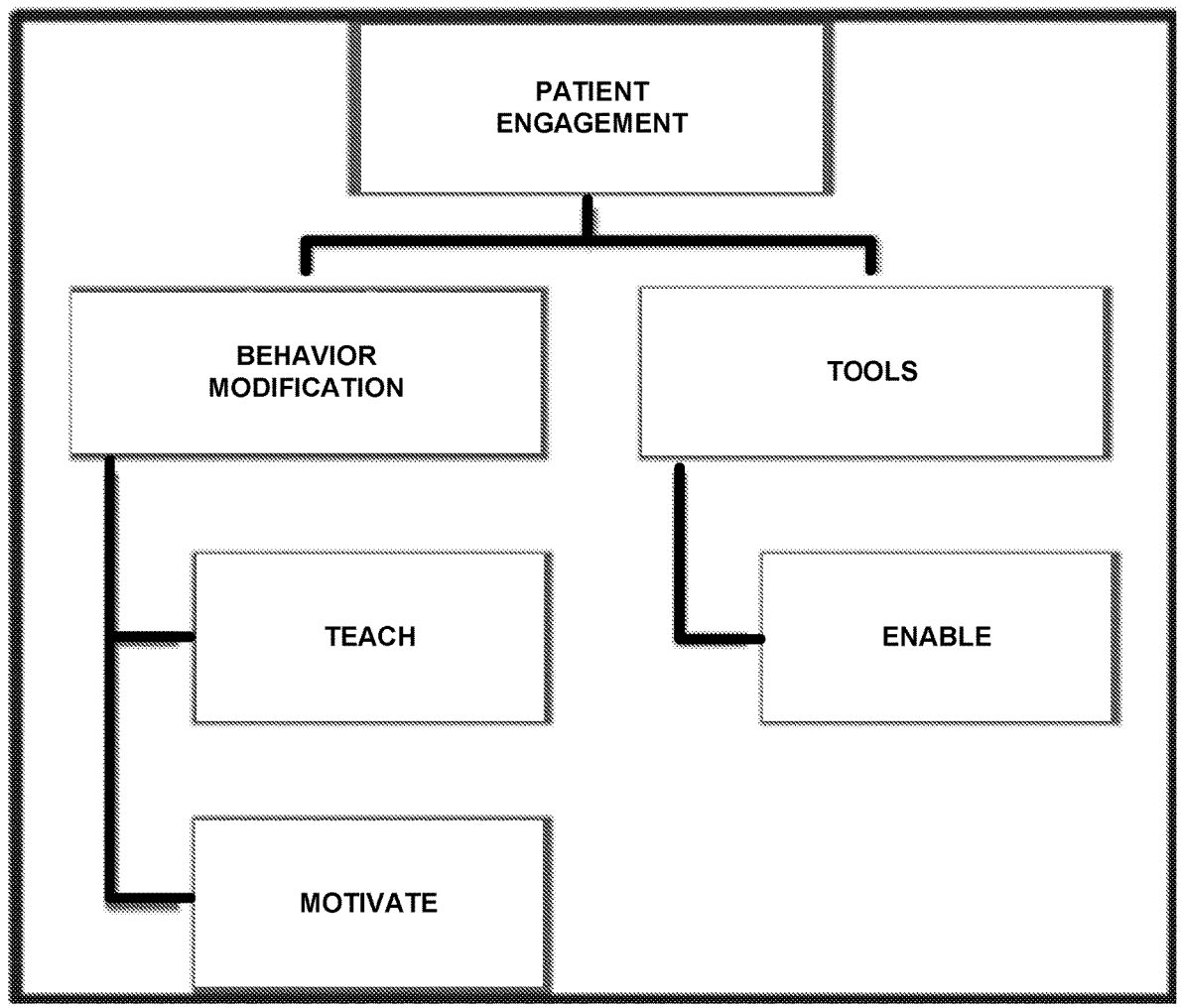
FIG. 3 is a schematic block diagram of an illustrative model employed by systems, methods and structures according to aspects of the present disclosure.

Operationally, eko-U generally employs an information-motivation-strategy (IMS) model to help drive patience adherence. FIG. 3 is a schematic block diagram showing the illustrative IMS model employed by eko-U. We note that an implementation of a teaching, motivating, and enabling methodologies—such as that according to the present disclosure—is configured to enable and reinforce one another.

This reinforcing relationship and its importance will become apparent to the reader of this disclosure.

Patient Engagement

To elucidate patient engagement elements of eko-U, we now consider the OCP example discussed previously. In an illustrative use case, the patient downloads eko-U's mobile application software for OCP adherence—the GINGER-U® application—on her mobile device. During the process of registering the application, the patient inputs various personal details (e.g., age, weight, nickname, etc.), as well as the identity of any medication (e.g., name, dosage, etc.) for which tracking is desired. In some cases, the identity of the medication is downloaded to the application via another method. Alternative methods for providing this information to the GINGER-U® application including, without limitation:

i. downloading it automatically from the cloud or other database in response to the issuance of the prescription by a healthcare provider who is registered with the application; or ii. downloading it automatically from the cloud or other database in response to the filling of the prescription by a pharmacy that is registered with the application; or iii. upon scanning of the medication label by the user with a smart phone or equivalent device, where the identity of the prescribed medicine is determined by text recognition, a digital watermark, barcode, etc.; or iv. any combination of i, ii, and iii.

Upon completion of the registration process, the user is provided with a "Profile" screen, which is personalized for the patient and the pertinent medication. An illustrative example of a Profile screen according to aspects of the present disclosure is shown in FIG. 4.

We note that with respect to illustrative examples so-far described herein, it is assumed that the GINGER-U® application works in conjunction with a smart pill case, such as those described in U.S. patent application Ser. Nos. 15/170,121 and 15/223,779—an illustrative example of which is shown in FIG. 2. In such a scenario, a patient will typically acquire such a pill case herself or obtain it in some other manner (e.g., it is provided by the pharmacy, doctor, other third-party, etc.). As will be understood and appreciated by those skilled it the art, such smart pill case connects to the patient mobile device via Bluetooth—or other mechanisms including both wired and/or wirelessly—(e.g., cellular, WiFi, etc.) to connect via an Internet. While not expressly discussed at this point, we note that the eko-U mobile application software may be advantageously customized for a particular affliction, disease, disease category as identified by an underlying code. For example, heart disease, diabetes, etc., may all be identified by such unique code.

In the OCP illustrative example specifically discussed herein, the patient's primary interface with eko-U is the GINGER-U® application running on her mobile device. And while a smart pill case will augment the overall patient experience, it nevertheless will likely provide a more limited, input/output/user interface capabilities. Furthermore, since mobile devices have become quite ubiquitous with persons/patients at all time(s), patient engagement with such a device is quite natural. Accordingly, key patient engagement provisions to facilitate/monitor OCP adherence are advantageously realized—according to aspects of the present disclosure—via the GINGER-U® application. We note that other illustrative examples of pill cases may eventually incorporate more extensive/comprehensive user interfaces (such as displays, speakers, microphones, etc.)—that may provide for a more "stand-alone" operation of such cases that will include certain functionality disclosed herein as a "front end", while still employing certain "back end" functionality to further facilitate/drive patient medication regime adherence.

Patient Education

We now consider another particularly advantageous aspect of systems, methods, and structures according to the present disclosure—patient education. As will be readily appreciated by those skilled in the art, patients are oftentimes not well informed about a therapy and/or medication regime they are contemplating and/or undergoing and may not fully appreciate the importance of adherence to the prescribed regimen. Most patients in fact do not even know what adherence means.

Unfortunately, physician and/or other provider appointment duration is usually not long enough for sufficient transfer of such information from provider to patient. Patients also tend to forget the information and instructions covered during the appointment. Furthermore, lack of adherence can be intentional, i.e., because of deficiency in understanding risks and side effects. As mentioned earlier in the context of OCP example, most patients know they have to take remedial steps when they miss a pill, but few know what such remediation entails. As noted previously, only 10% of all OCP patients know that missing just one pill places them at risk of pregnancy!

We note that advantageously our eko-U application teaches the patient about the medication and adherence during "onboarding". Note further that the term "onboarding" refers to an initial process of registration for a personal account after downloading application software.

A patient may advantageously recall this information as needed and dive deeper into learning as desired by further interaction with the mobile application. Of further advantage, the information that may be provided by the mobile application is not limited to that stored locally on the mobile device. Advantageously, and according to further aspects of the present disclosure—such information provided by the mobile application may be stored in a "cloud", or retrieved by any of a number of known mechanisms that provide private/and/or/public networking/internetworking or applications built thereupon including hypertext driven ones such that the world wide web.

The specific teaching/reference information that eko-U curates and serves in this regard is generally related to the following—for which the patient would need to know existence and discovery (e.g., Web search), otherwise:

1. Terminology
2. Importance of adherence
3. Manufacturer's Label
4. Library of similar medications
5. Frequently asked questions We note that this information is generally particular to a particular disease and incorporated into the disease-related application software. It is also particular to the medication. It can be provided in the form of easy text, graphically and/or by animation.

We note further that—in sharp contrast to any prior-art, systems, methods, and structures according to aspects of the present disclosure exploits any information provided by the manufacturers label—including inserts—for a medication as the touchstone for many aspects of regimen adherence, including customization/particularization to a specific medicine and its therapeutic regime(s), as well as an individual patients side effects. It should be noted that prior-art medicine regimen adherence approaches will ignore the manufacturer's label. By exploiting this information, the present invention enables the patient to be provided proper dosage information, proper remediation actions, information about alternative medicines, and the like. In addition, systems, methods, and structures according to the present disclosure enables this information to be kept current by providing for automatic downloads of changes to the regimen as they issue from the FDA (U.S. Food and Drug Administration), the manufacturer, and the like.

Figure 6A:
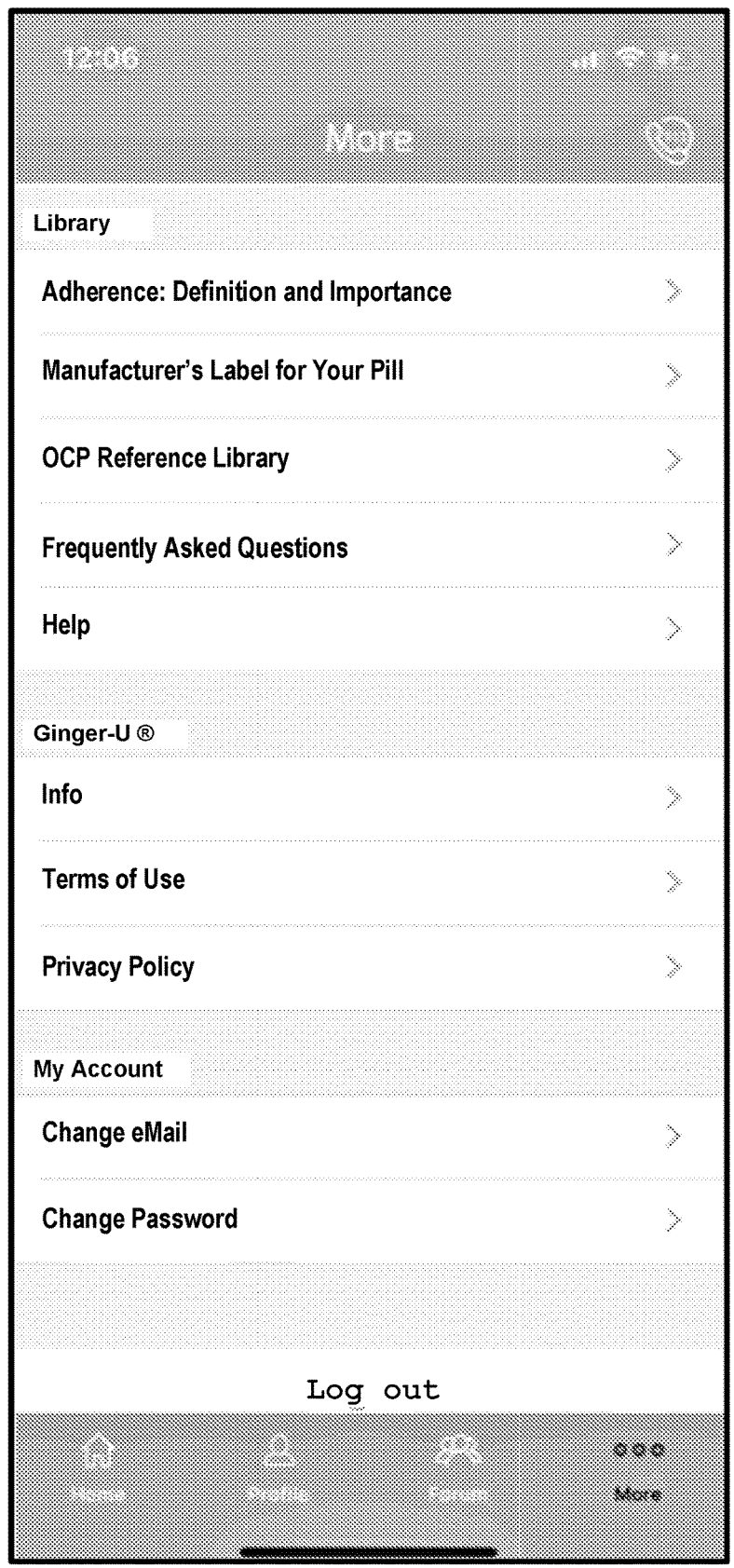
FIG. 6(A) and FIG. 6(B) are illustrative application internal screens about.
Figure 6B:
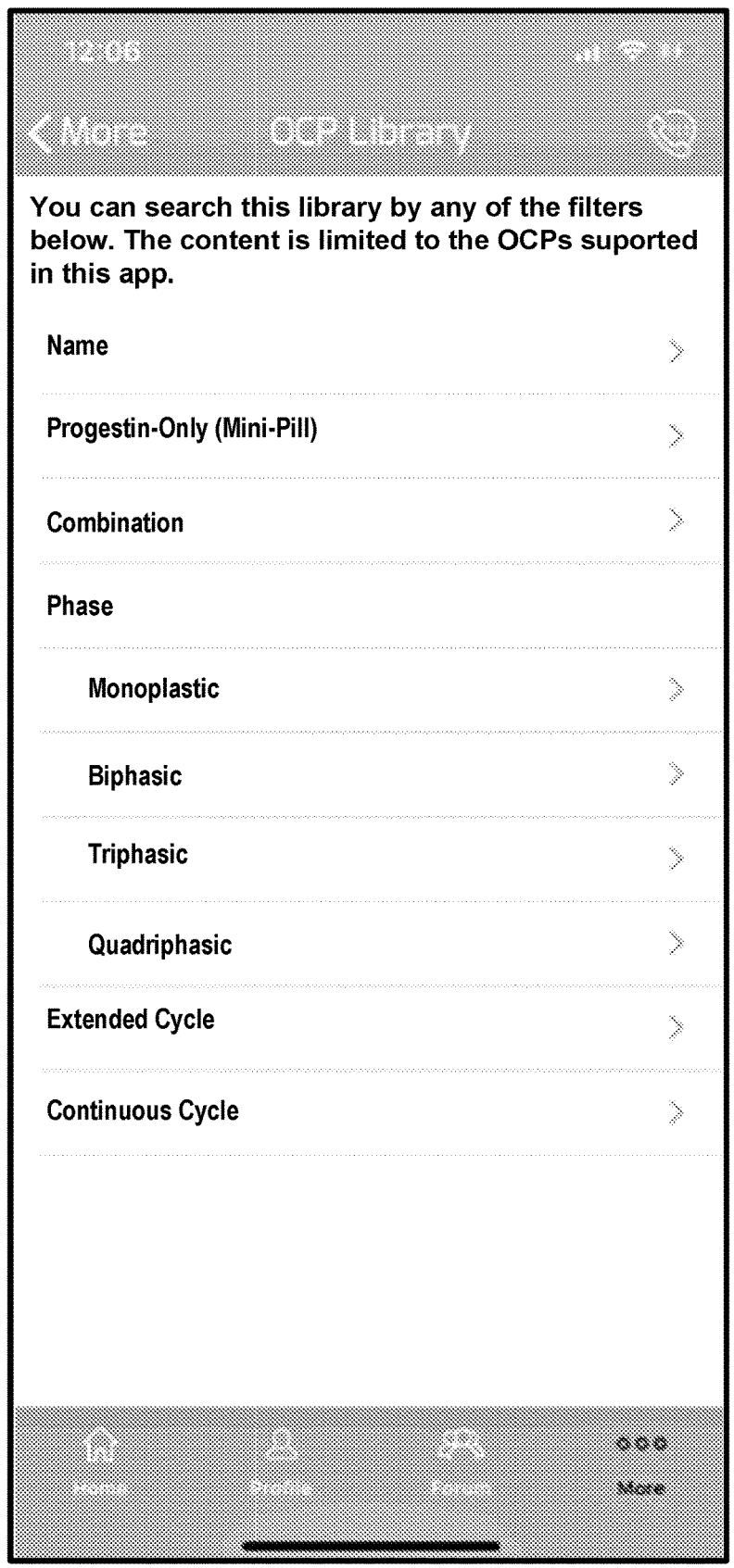

Turning now to FIG. 5(A), and FIG. 5(B), there is shown illustrative screens from the GINGER-U® application onboarding for Items 1 and 2 (above). Similarly, FIG. 6(A) and FIG. 6(B) shown illustrative screens from the GINGER-U® application internal recall tabs for Items 3, 4 and 5 (above).

We note that any governing instructions and information for any medication (e.g., descriptions of usage, dosage, health benefits, side effects, precautions, etc.) are documented in its manufacturer's label or insert—something patients usually do not even know exists. Advantageously, illustrative implementations of systems, methods, and structures according to aspects of the present disclosure provides patient access to it by clicking the "Manufacturer's Label for Your Pill" tab on the illustrative screen shown in FIG. 6(A). Similarly, clicking the "OCP Reference Library" tab provides the patient the screen illustratively shown in FIG. 6(B). The library enables the patient to learn about OCPs—and compare and contrast them. The "Frequently Asked Questions" tab lead to a screen with answers to questions like "How do OCPs work?", "What is the Manufacturer's Label?", "What do I do if I mistime/miss one or more pills?", "Which OCP is best for me?", etc.

Through teaching, eko-U and systems, methods, and structures according to aspects of the present disclosure advantageously provides the patient (i) with an understanding of what to achieve and why, and (ii) with sense of personal control over the situation. Doing so is important to set the stage for motivation.

Figure 11:
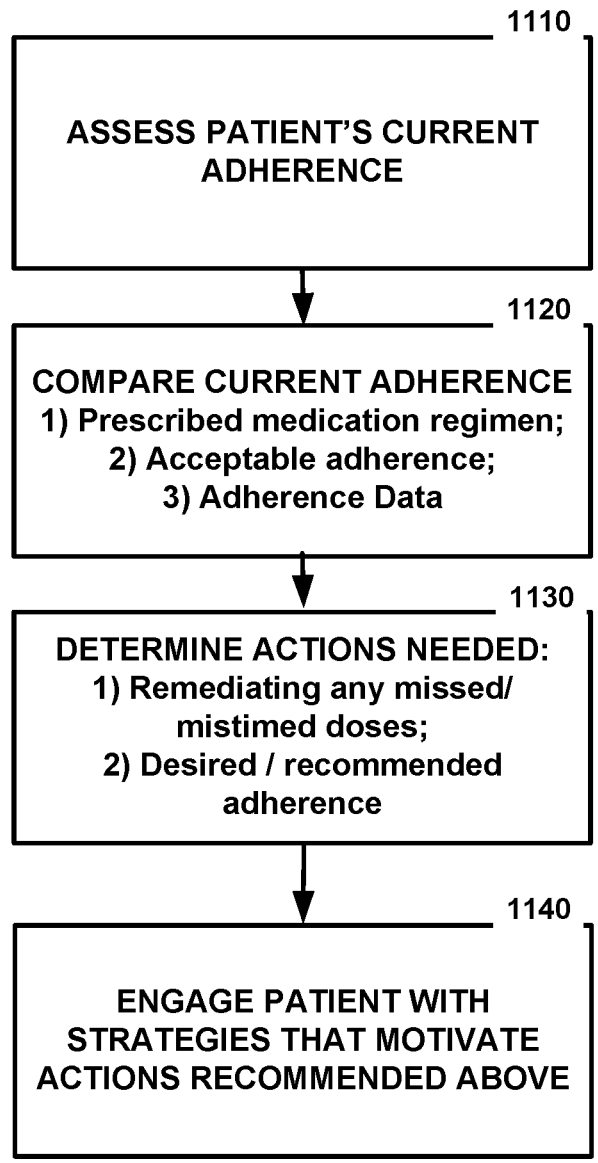
FIG. 11 is an illustrative flow diagram showing steps associated with patient compliance and remediation action(s) according to aspects of the present disclosure.

As will now be readily understood and appreciated by those skilled in the art, eko-U and systems, methods, and structures according to the present disclosure motivates a patient by monitoring adherence (i.e., using the adherence infrastructure described previously in the related Patent Applications incorporated herein by reference—namely, U.S. patent application Ser. Nos. 15/170,121 and 15/223,779) and accordingly effectuating commitment to adherence. It uses a dynamic method based on a patient's ongoing adherence. This method is built the following sequence of steps as outlined in a flow diagram of FIG. 11:
1. Assess the patient's current adherence
2. Compare the patient's current adherence to the
   a. Prescribed medication regimen adherence
   b. Acceptable adherence for the medication/therapy
   c. Patient's adherence data (accumulated) to date
3. Determine actions needed for
   a. Remediating currently missed/mistimed doses
   b. Desired/recommended adherence behavior
4. Engage the patient with strategies that motivate taking the actions of Step 3

The initial data used in Step 1—Block 1110—is generally gathered from the patient during onboarding. Later in this discussion, we will describe some additional onboarding data that may advantageously be collected from a patient/user and subsequently employed during operation of the compliance/adherence regime.

With simultaneous reference to FIG. 7(A) and FIG. 7(B) there it shows an example screen of the GINGER-U® application that gathers illustrative information for the OCP example. Based on the answers provided by the patient, the GINGER-U® application places the patient in one of three adherence categories: "Perfect Adherence"; "Typical Adherence"; or "Poor Adherence". (For OCP efficacy, anything below typical adherence is poor, i.e., leads to high risk of pregnancy.) As we shall show and describe, information gathering questions may be modified or different. Accordingly, different data gathered will provide some additional advantageous capabilities.

Once the patient/user is categorized, the GINGER-U® application suggests adherence support options, e.g., reminders, personalized reminder messages, reminder buddies (discussed below), etc.

We note that there is no "gold" standard for adherence quality. By comparison, eko-U's quality classification formulation (i.e., perfect, typical, or poor) is unique, simple, and rational. Anyone with less than typical adherence is showing poor adherence. In contrast, it may be understood that different medications may merit eliminating or adding (e.g., "Good", "Fair", etc.) classification, and/or using a numerical adherence score. These classifications may however confuse what adherence level is expected. In eko-U's classification, typical adherence is the minimum adherence level expected.

Note that the foregoing adherence categorization is a quasi-static behavioral indicator, determined based on accumulated adherence data over a preceding time window. A patient's adherence category may change depending on changes in adherence behavior analyzed over such time window. Accordingly, the factors considered for such are:
   Number of missed and mistimed pills
   Time distribution of missed and mistimed pills
   Nature of missed and mistimed pills (e.g., some pills may be placebos)
   Time window spanning occurrences In addition to the quasi-static indications noted above, eko-U and systems, methods, and structures according to the present disclosure also performs a dynamic adherence determination. This dynamic adherence tracking indicates if prescribed regimen is being followed. For example, a "Typical Adherence" patient is not adherent on the day she misses her pill, even though this one miss (by itself) may not affect her quasi-static behavioral categorization.

Figure 7C:
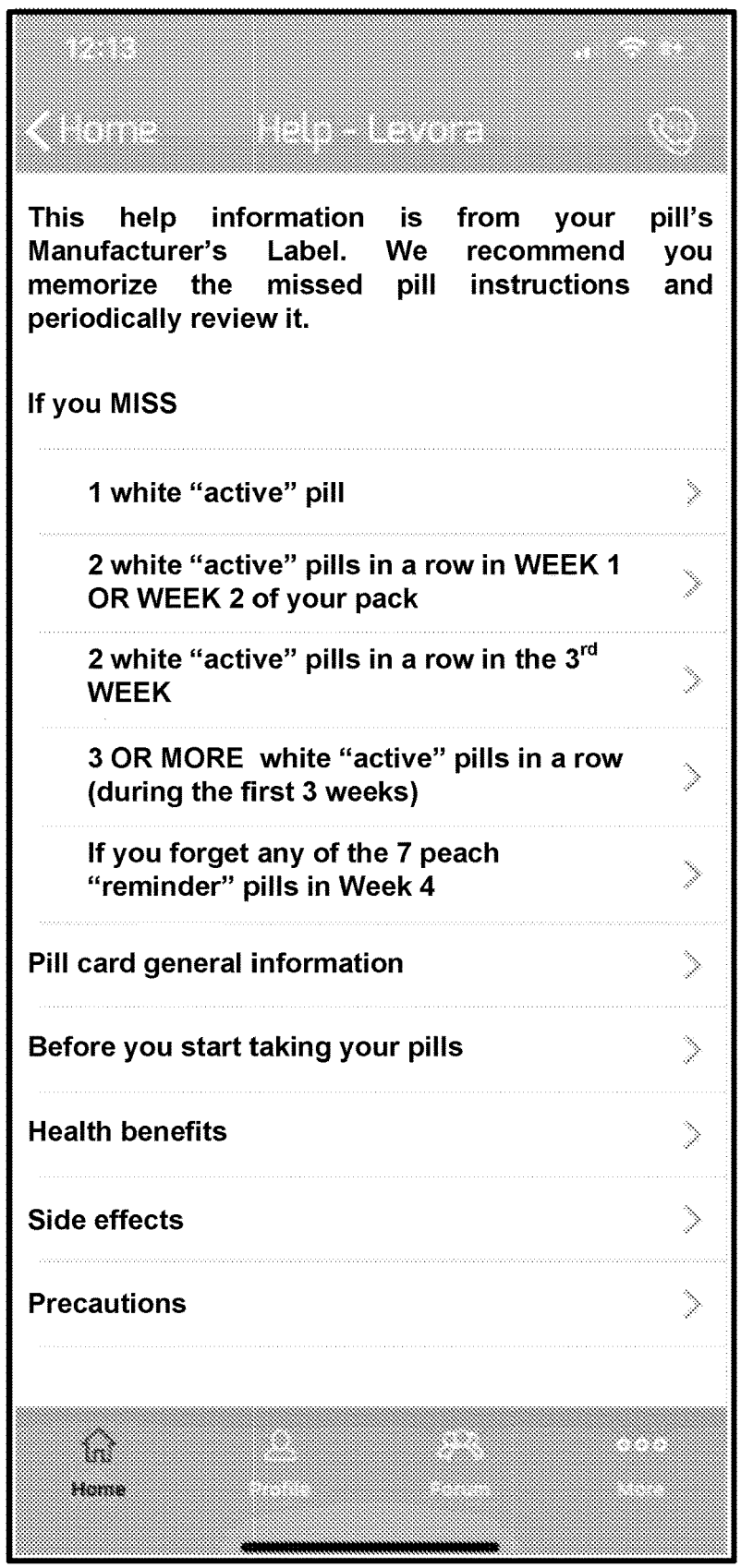

The dynamic adherence data used in Step 2—Step 1120 may come from the smart devices used by the patients (e.g., the smart pill cases described in U.S. patent application Ser. Nos. 15/223,779 and 15/170,121, other prior-art pill tracking approaches, etc.)—in addition to user entry. The comparative reference data for this step comes from the curated information (described earlier) for adherence, particularly the Manufacturer's Label—insert. OCP adherence guidelines—used here as an example—are complicated in comparison with other medications and very specific as to remedial steps for missed/mistimed doses. FIG. 7(C) shows the help screen from the GINGER-U® application, which accounts for various related adherence lapses scenarios.

As will be understood and appreciated by those skilled in the art, with OCP, dynamic adherence assessment is in a ~24-hour daily window. For example, missing today's pill makes the patient not adherent, but taking today's missed pill with tomorrow's pill makes her adherent again. However, taking tomorrow's pill tomorrow, but not today's missed pill also tomorrow, keeps the patient not adherent.

Figure 8A:
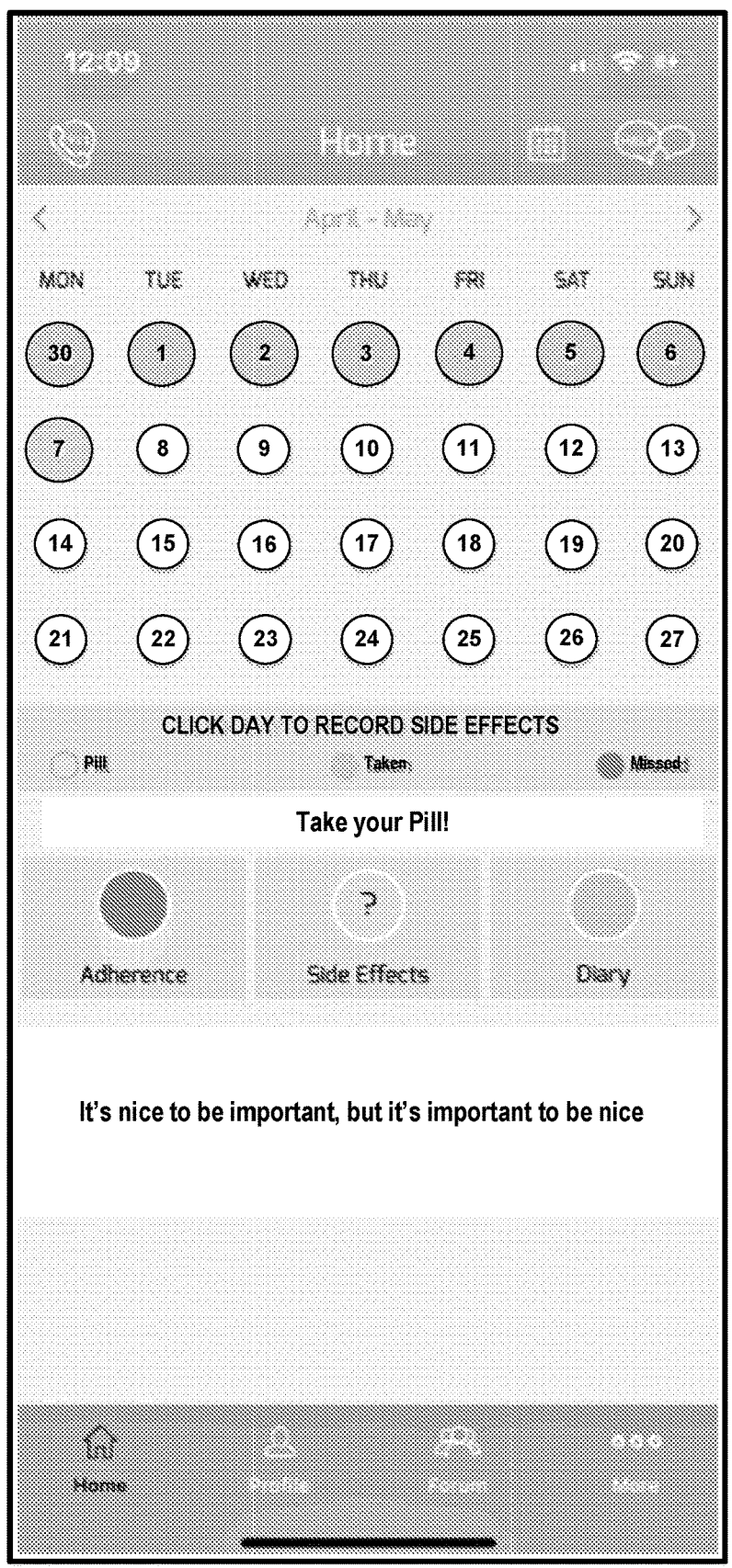
FIG. 8(A) and FIG. 8(B) are illustrative graphical application screens showing a patient's actual adherence with hyperlinks to additional helpful information according to aspects of the present disclosure.
Figure 8B:

In Step 3.—Block 1130—the GINGER-U® application compares the specific adherence guidelines of a given OCP with the actual adherence of the patient on a dynamic/ ongoing basis. The patient is made aware of her daily adherence status, as depicted in FIG. 8(A) and FIG. 8(B).

Figure 9:
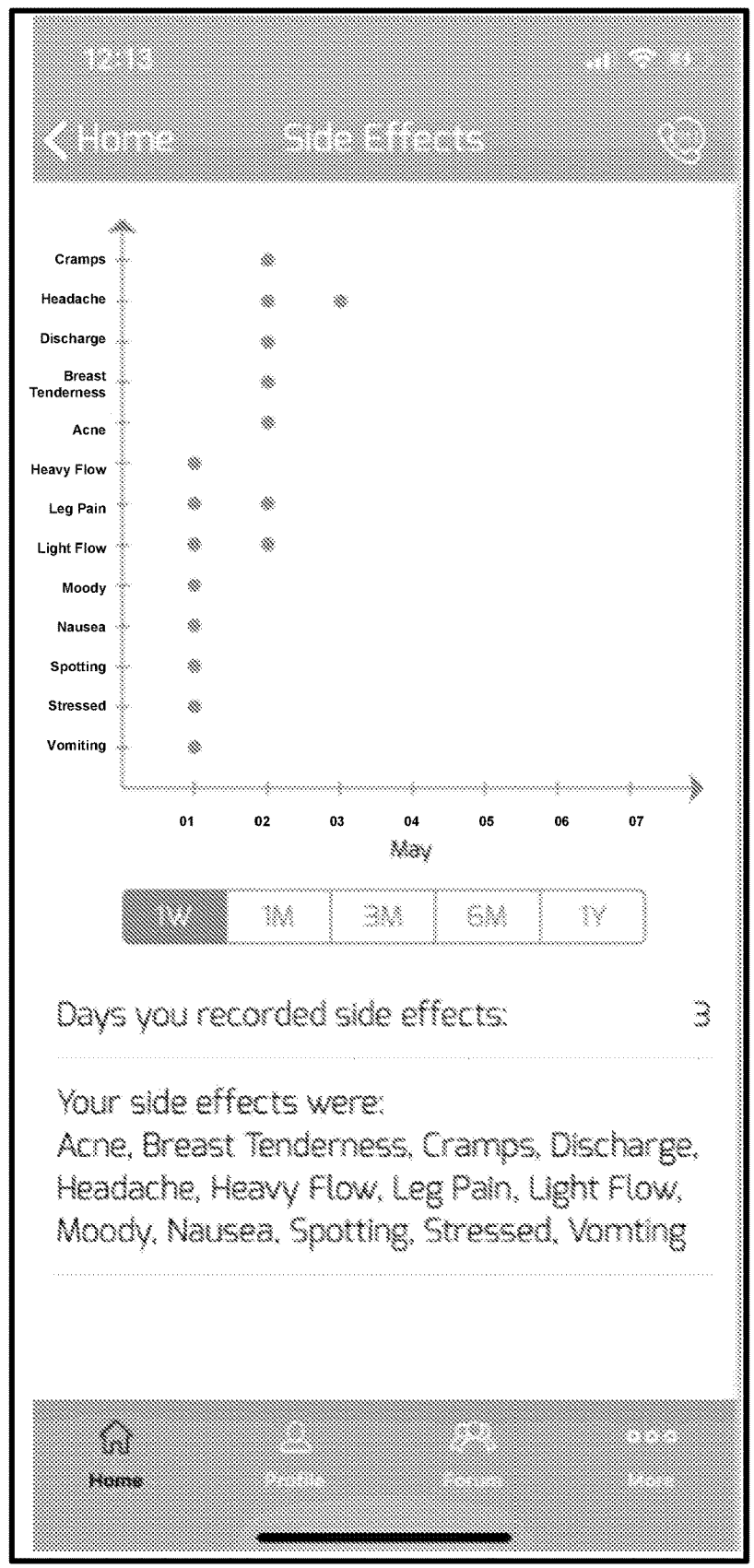
FIG. 9 is an illustrative application screen showing side effects diary for a patient according to aspects of the present disclosure.

Of further advantage, systems, methods, and structures according to aspects of the present disclosure provide for the recordation of any side effects for a particular medication regime as illustratively shown in FIG. 9.

When her daily adherence lapses, notifications are initiated through her smart phone with the GINGER-U® application and also appear on her smart device (e.g., flashing of the light emitting diodes noted on FIG. 2), when a smart device also used.

At Step 3—Block 1130—is an assessment of the patient's current adherence behavior versus that recommended for the medication. It accounts for both the dynamic adherence and quasi-static categorization. The assessment at this step is used to tailor effective strategies to motivate the patient in the right direction in Step 4.

At Step 4—Block 1140—the engagement strategies—for motivating patients in the right adherence direction—are deployed. These strategies are different (i.e., custom/tailored) for different scenarios. One lever in deploying these engagement strategies is through custom reminder/alert messaging of the mobile application. These examples are intended to elucidate the approach, using the OCP example/GINGER-U® application:

1. A patient in the "Poor Adherence" category will get:
   Encouraging messages like "Way to go girl!", "Look up, smile and recommit to adherence!", "You may day dream now", etc. when adherent.
   Stark messages like "What if you got pregnant?", "Do your plans include a baby?", "Can you support a baby?", etc. when not adherent.
2. A patient in the "Perfect Adherence" category will get:
   Validating messages like "Reach for the stars!", "Kiss the air and smile!", "Let your romantic side shine!", etc. when maintaining her streak.
   Supportive messages like "Make it up now!", "Keep your streak alive!", "Don't let your streak end!", etc. when missing a pill.
3. A patient in the "Typical Adherence" category will get:
   Encouraging messages like "Keep it up!", "First step in romance, checked!", "Great consistency!", etc. when adherent.
   Reminder messages like "Being safe is disarming!", "Ease of mind is a turn-on!", "Make it a good day!", etc. when now-and-then missing a pill.

Messages for different scenarios need not be mutually exclusive. For example, some of the respective messages in Items 2 and 3 can be used interchangeably. Furthermore, it would be clear to those skilled in the art, after reading this disclosure, that messages would be adapted for other disease states within their disease-specific mobile applications—as well as specifically tailoring such motivational message(s) for a particular patient/user.

At this point we note that our unique motivational framework outlined above defines/employs consideration of adherence as two distinct—but interrelated—elements (i.e., quasi-static and dynamic elements).

Yet another lever in deploying engagement strategies involves the employment of a care circle. It entails that people in the care circle to reach out to the patient. Since streaming adherence data to these persons in a care circle is generally not attractive to those persons, a more effective mechanism according to aspects of the present disclosure involves the timely provision of actionable alerts when needed (e.g., "Patient has not taken her pill today!"). Such alerts can be delivered automatically (e.g., with the GINGER-U® application for OCP) by call, e-mail, text message, and the like.

For providers, payers and pharmacists, even actionable alerts may not be practical outside of a clinical environment (hospital or other managed care facility where provider/patent are co-located) and/or attractive (because such support is not part of their business model).

According to aspects of the present disclosure however, the patient's affiliates/social network is an option. For example, the GINGER-U® application incorporates a "Reminder Buddy" feature. The patient has the option of designating one or more affiliates (e.g., spouse, parent, friend and/or even the professionals from the care circle) to receive actionable alerts. The reminder buddies will then reach out to the patient as needed. The GINGER-U® application requires acceptance confirmation from reminder buddies for their role.

Alerts issued by the GINGER-U® application need not be limited to when the patient has not taken her daily pill. The patient may choose to send confirmation alerts every time she takes her pill—a feature that can also be used as a daily (safety) beacon for the patient. The patient may choose to share more extensive adherence data and analysis with her reminder buddies (and/or care circle people) as she sees fit.

Yet another lever for deploying engagement strategies is through a reward approach. The gaming industry uses rewards for user engagement exceptionally well. As is generally known in the art, leveraging the power of games to affect health behavior has been discussed in detail in "Wireless Health: Remaking of Medicine by Pervasive Technologies—Chapter 16" edited by M. Mehregany and published in 2014 by AuthorHouse, which is incorporated herein by reference. Games provide rewards in the form of points, levels, badges/achievements, earned rewards, etc. Their rewarding approach is direct and immediate.

Rewards are used in a variety of industries to affect behavior. Examples include loyalty programs such as frequent flyer miles with airlines and points/cash backs with debit/credit cards. For medication adherence, there are currently instances of points reward systems, wherein the points are then used to receive benefits from the payer and/or the pharmacy. The effectiveness of these reward strategies for medication adherence is limited, however, because immediate, palpable conversion to an actual benefit is missing in these strategies. For example, many forego accumulating a particular frequent flyer program by opting to buy a less expensive, a direct, an earlier, a later, etc. flight on another airline. Similarly, a patient may find different reasons to forego points related to adherence quality in favor of other more immediate benefits.

In comparison, sales/discounts and rebates are used for immediate motivation. Their adaptation to medication adherence motivation is exploited in eko-U. The methodology is to offer the patient purchasing options in eko-U's mobile applications, wherein the options are based on the patient's adherence. In other words, the purchasing options' (i) quality and/or quantity, and (ii) associated discounts are a function of the patient's adherence quality. The menu of purchasing options changes dynamically to correspond to the dynamic adherence requirements of specific medications and therapies. This approach generates anticipation (i.e., the patient would want to know what options will become available next); unexpected awards are known to be more powerful for behavioral change than expected awards. Each patient will see the purchase options available to her/him, as well as options were she/he had better or worse adherence.

This approach motivates improving one's adherence to get better purchasing options or maintain good adherence not to be downgraded in options.

Let's elucidate the foregoing using the OCP example. In this case, the patient population comprises women 15 to 45 years old, defining the market sector. Purchase-option menus with beauty, health, fashion, sex and the like products/services items would likely be quite relevant. Nevertheless, options need not be limited to these; for example, women shop for the entire household, substantially expanding the options space. In theory, the purchase options may be anything. With OCP, adherence typically requires a daily dose. Accordingly, the menu of options is modified on a daily basis to drive anticipation and deliver surprises, i.e., in order to move the patient's adherence in the right direction. To facilitate this approach, the GINGER-U® application has in-app purchasing functionality.

Another lever for deploying patient engagement strategies is through competition. In this case patients compete for adherence. In a particular illustrative implementation, eko-U facilitates organizing a social circle for such adherence competition. The adherence information driving the competition is then shared among the patient group per user-defined guidelines of the competition. For example—for OCP—the competing group may designate assessment of adherence based on if and exactly at what time the daily pill is taken. Similarly, the group may decide to share this data among the competing members daily, periodically, at the end point of the competition, etc.

The approaches described above are based on gaming theory. For example, the quasi-static adherence categorization of a patient by eko-U is assigning a mastery level. It motivates the patient to want to move to a higher level. The alert/reminder messages are direct and immediate feedback on achievement (or lack thereof). The purchase option rewards are like earned currency. Social network engagement is being part of a community. Competition is an inherent element of games.

As will become apparent to those skilled in the art upon review of this disclosure, payers may structure consequences of cost coverage by use a patient's adherence data. These consequences may be rewarding for good adherence, using one or more of the approaches discussed above. On the other hand, they may be punitive for poor adherence, i.e., taking benefits away from the patient. Rewarding is more effective than punishing in affecting behavior. In addition, punitive approaches trigger sociopolitical liabilities.

Tools eko-U in and of itself is a composite of tools to enable the patient to pursue good adherence. Many of these tools have been elucidated in the context of the topics and concepts described above. A few more are described here.

One unique tool in eko-U's disease specific mobile applications accesses the patient's calendar to anticipate potential adherence challenges. For example, a patient may be about to depart for a calendar event that extends into or beyond her/his next dose time(s). The patient will be reminded to take the medication along. In some cases, a calendar event accessed by eko-U includes the name of a person or place whose address is contained within the contact list of the user's smart phone (or other device). In some embodiments, the distance to this address is computed (via a map application, etc.), as well as the time required to travel this distance from the current location of the smart phone. A spatial-temporal correlation of the current location of the smart phone, the current time, the location of the calendar event, the time of the calendar event, and traffic pattern data, is then made to determine a time at which a reminder should be provided to the user to, for example, remind her to pack her pill (or pill case) so that she has it when attending the calendar event.

Another unique tool uses the smart phone location to assess the patient's distance from her/his medication. The smart device containing her medication may also incorporate location-identifying capabilities like a smart phone. Alternatively, the smart phone may record the last location of its Bluetooth connectivity to the smart device and test to assess if the smart device is in Bluetooth range or not. The patient can be alerted regarding an upcoming dose with earlier if the medication is not in the range of the smart phone. In some cases, a reminder is generated based on the travel time between the current location of the phone and the desired time for the upcoming dosage to give the user an opportunity to get access to the medicine in time for proper dosing. In some embodiments, the current location of the pills is provided to eko-U by a smart pill case that has geolocation and communication capability and that location is also factored into the calculation regarding the time at which a reminder is generated.

Combining the foregoing two tools enables alerting a patient that is departing for a calendar event without his/her medication, if there would be a dose time(s) in the interim. Alternatively, the patient may be alerted to leave for the location of the medication for timely administration of the next dose. The lead-time of this alert can be estimated from the map/traffic mobile application on the patient's smart phone.

Another aspect of the present invention is a tool that enables auto-refill and auto-appointment—capabilities incorporated in eko-U by leveraging the care circle connectivity and adherence monitoring from the smart devices. Refills are a contributor to adherence lapses. Patients forget or neglect to act timely, because there is effort involved. Auto-appointments can be used to schedule visits to discuss adherence importance and understand a patient's challenges to be adherent.

With respect to OCP for example, studies show that adherence is improved when patients are given a three-month supply instead of a one-month supply. Since the GINGER-U® application and its related smart pill case track adherence, they can provide timely refill reminders. Better yet, the GINGER-U® application enables an auto-refill capability, wherein the new supply can be received as shipment or picked up at the pharmacy.

Figure 10:
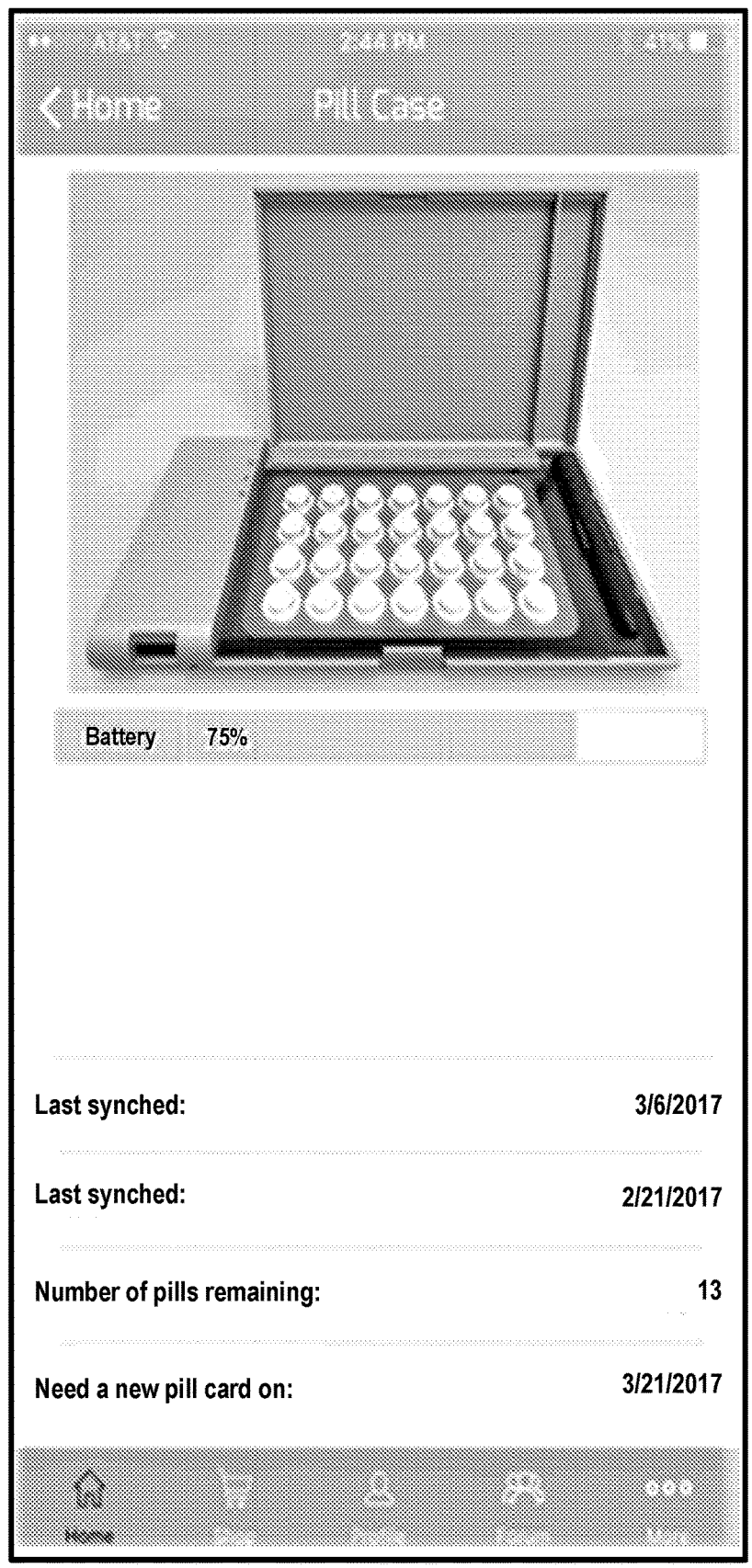
FIG. 10 is an illustrative pill case screen showing current status of the pill case to which the application is registered according to aspects of the present disclosure.

Advantageously, eko-U's disease specific mobile applications also provide diaries for side effects and related notes. The diary tool shown illustratively in FIG. 10 enables tracking side effects and correlating the causes. The diary tool can tap other health and wellness mobile applications on the patient's phone for additional data to support its correlation analysis.

Of further advantage, eko-U's disease-specific mobile applications incorporate an in-app shopping tool. This shopping tool facilitates purchases in support of the strategies described above.

It should be noted that some of the software functionality in eko-U is resident on the smart devices in the form of firmware running. The microprocessor in the smart device provides for local computational functionality to implement the requisite algorithms for the designed capability. For a smart pill case, these algorithms include, for example, detection of pill dispense event and related time stamps, audio/visual alerts on the device, indication of adherence on the device, indication of battery life, etc.

As we have so far described with respect to an OCP regime, the adherence systems, methods, and structures illustratively described have employed the smart pill cases. We note at this point once again that such smart cases/dispensers are not a requirement of systems, methods, and structures that are contemplated herein.

Manual Patient/User Inputs

Figure 12:
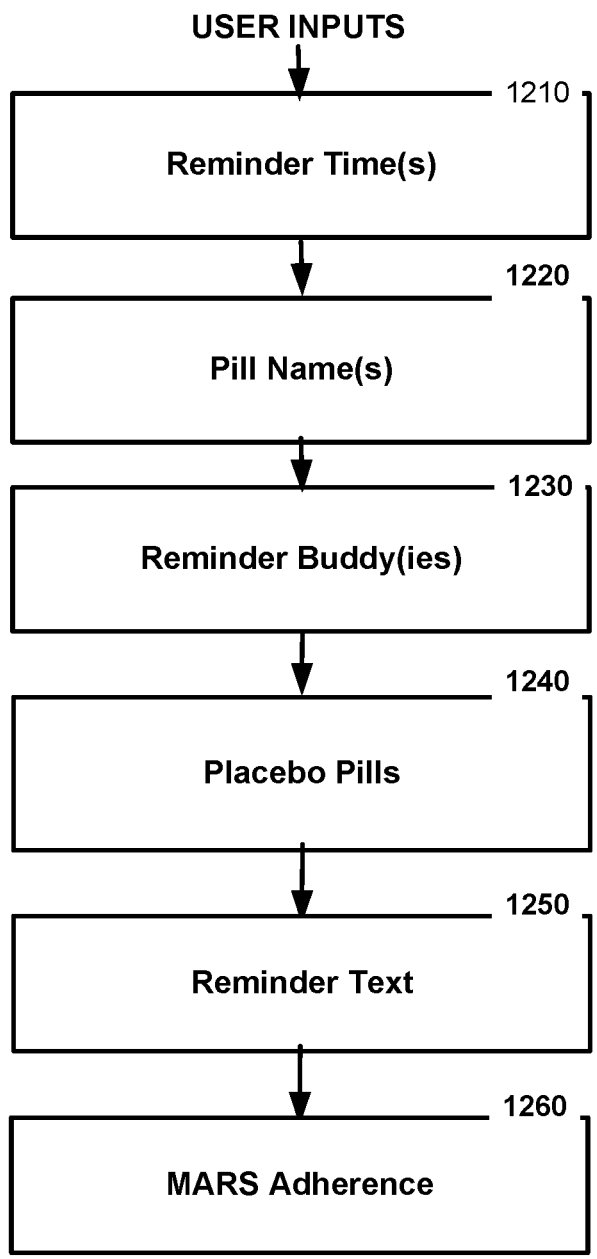
FIG. 12 is an illustrative flow diagram showing manually entered data during illustrative onboarding according to aspects of the present disclosure

When smart pill cases/dispensers are not employed, much of the data related to user/patient setup that is employed by systems, methods, and structures according to aspects of the present disclosure may be provided by manual user input during onboarding. By way of illustrative example only, and with reference to FIG. 12 which shows illustrative user input data including: 1210 Reminder Time(s), 1220 Pill Name(s), 1230 Reminder Buddy(ies), 1240 Placebo Pills, 1250 Reminder Text(s), and 1260 MARS (Medical Adherence Rating Scale) Adherence Questions.

Figure 13:
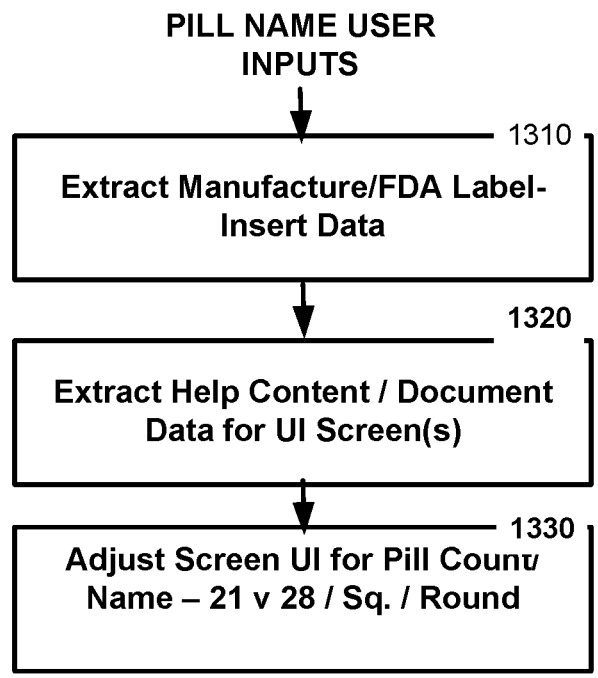
FIG. 13 is an illustrative flow diagram showing manually entered data pill name/pill ID during illustrative onboarding according to aspects of the present disclosure.

FIG. 13 is an illustrative flow diagram showing illustrative pill name/pill ID data utilization. After a user/patient enters a pill name, a number of processes follow. At Block 1310 the manufacturer's/FDA label-insert specific data to the pill—from the pill name or other identifier provided—is extracted. Any help content/document specific information specific to the pill is extracted from that label-insert or other on-line or local data sources at Block 1320. Such data is made available and/or inserted into any appropriate help/home/operational application screens. Finally, at Block 1330, additional adjustment to screens is made based on pill count for the specific medication regime. As specific non-limiting examples with respect to OCP, a pill card may include 21 or 28 individual pills, the card may be square or circular, etc. Advantageously, the screen(s) within the application may be made to correspond to these characteristics once entered.

Figure 14:
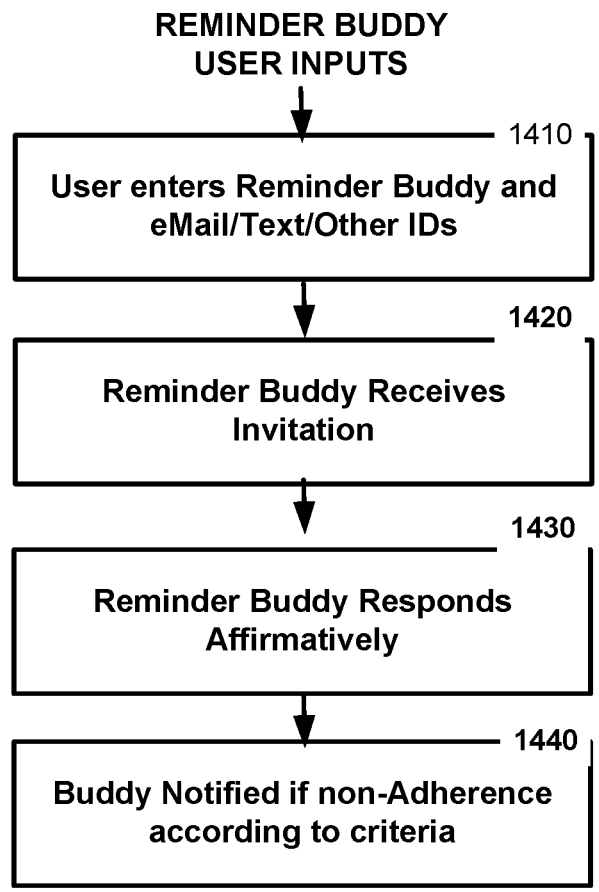
FIG. 14 is an illustrative flow diagram showing manually entered reminder buddy data during illustrative onboarding according to aspects of the present disclosure.

FIG. 14 is an illustrative flow diagram showing illustrative operations associated with the identification of a reminder buddy (i.e., a patient affiliate) during onboarding—or thereafter. As shown in that figure, at Block 1410 the patient/user provides the name of any Reminder Buddy(ies) and their eMail/Text/Other notification ID. Such notification IDs are addresses to which non-adherence notifications will be sent if non-adherence is detected by systems, methods, and structures according to aspects of the present disclosure. As will be known and appreciated, when such Reminder Buddy is notified, that person may take affirmative action such as contacting the patient to encourage adherence.

Upon identification of Reminder Buddies, the buddies are invited to participate at Block 1420. If the buddy agrees to participate, then an affirmative response is made at Block 1430 via return eMail, Text, or other mechanism. Once the buddy relationship is established, a non-adherent patient will trigger a buddy notification who—in turn—may encourage adherence by the patient.

Figure 15:
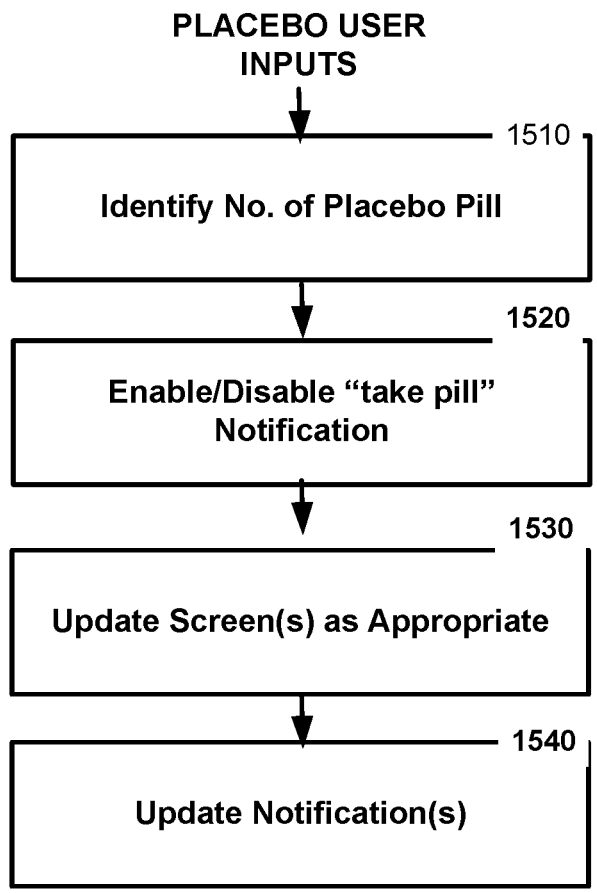
FIG. 15 is an illustrative flow diagram showing manually entered placebo data during illustrative onboarding and operational changes according to aspects of the present disclosure.

FIG. 15 is an illustrative flow diagram showing illustrative placebo data user inputs and operational aspects of systems, methods, and structures according to aspects of the present disclosure that follow such input. During onboarding, a user/patient will select or de-select an option where placebo is established. Based on the selected pill name and the placebo choice, at Block 1510 the number of the placebo pills are determined. Also, at Block 1520 enable/disablement of the "take your pill" notification is made depending upon whether or not a placebo is included on any pill card currently used. At Block 1530, any application screen(s) that utilize placebo information are updated and correct date/pill are maintained. By so doing, a user knows what day of the pill card she is using and how many more placebo pills remain in her current card—if any. Finally, at Block 1540 additional screens/notifications are disabled. For example, no blinking in a User Interface if notifications are disabled if such disablement is selected.

Reminder Text: As noted previously, reminder text/sentence is provided/entered by the user/patient. In an illustrative embodiment, such text is the user's choice that is displayed as a daily—or other interval—notification.

MARS Adherence: During onboarding, a user will answer a number of questions—currently 5—that help determine adherence history and drive subsequent reminder timing determinations and generate an illustrative MARS score. In illustrative embodiments, such timing is only for before-you-take pill reminder notifications. Illustratively, such notification may follow adherence.

By way of illustrative example, adherence may be assigned to levels of adherence namely, Good, Poor, and Perfect. If a user/patient exhibits Good adherence (score 85-90), such notification time may be equal to the reminder time—5 minutes—or so. Poor adherence (score<80) notification time may be equal to the reminder time—15 minutes. Finally, Perfect adherence (score>=90) results in a notification time equal to the reminder time. As one can determine from this discussion, the more adherent a patient/user is, the closer to the reminder time the notification may occur. Conversely, when a patient/user exhibits poor adherence, their reminder time will include an additional 15 minutes so that adherence is more likely.

Reminder Time: With respect to the user reminder time, the user will choose during onboarding a reminder time when she would like to take her pill(s). Things to consider when contemplating a reminder time and considered according to systems, methods, and structures according to aspects of the present disclosure include:

1. Assume a sleep-time between 11 PM and 7 AM;
2. Sleep factor is assumed to occur for 8 hours/day;
3. Wake cycle is assumed to be 16 hours/day;

Accordingly, the pill taking time for any user/patient is assumed to be between 7 AM and 11 PM. Obviously, and advantageously, users may readjust this based on when the user chooses her reminder time(s). Alternatively, the user may provide specific sleep times—particularly when sleep patterns are changing. Note that based on the wake cycle(s), notifications may take place only during those times. In this manner, the user/patient is not bothered during sleep periods. Accordingly, alerts or messages or any local notifications only have to be active during wake cycle(s) and inactive during sleep cycle(s).

Operationally, systems, methods and structures according to aspects of the present disclosure may perform a number of adherence calculations. In very specific illustrative implementations, such adherence may employ:

Step 1:
   Only use MARS questions;
   Based on user answers, scale is from 5-25;
   Transform to % (100-MARS)%;
   Perfect=90-95%
   Good=85-89%
   Typical=8-84%
   Poor=<80

Step 2:
   Week Wise
   ($3/4$ Step 1)+$1/4$ week 1)=step a;
   ($1/2$ Step a)+($1/2$ week 2)=step b;
   ($1/4$ Step b)+($3/4$ week 3)=step c;

For every missed pill, subtract 100/7 from a 100

Month Wise

Similar to week-wise, but adherence will reflect the real-time value and not week-wise.

Step 3:

$1^{st}$=month−1;

$2^{nd}$=½ $1^{st}$+½ month−2;

$3^{rd}$=¼ $1^{st}$+¼ $2^{nd}$+½ month−3;

$4^{th}$=¼ $2^{nd}$+¼ $3^{rd}$+½ month−4+½ month−5l;

$6^{th}$=¼ $3^{rd}$+¼ $5^{th}$+½ month−6.

Missed Pill Push Notifications Sequencing: Illustratively, we now describe three types of push notifications: 1) Notifications prior to reminder time; 2) Notifications after reminder time; and 3) Notifications to alert user to open application after a period of no usage.

In illustrative embodiments, timing considerations for notifications prior to reminder time may occur at 5 or 10 minutes before actual reminder time based on adherence history of the user/patient. If the reminder time has passed, timing to trigger notifications may follow those noted above assuming sleep assumptions. Unconditional notifications (when reminder time has passed and user has not taken pill) may proceed—illustratively—at reminder time+15 minutes; or reminder time+60 minutes—or other periods as appropriate and chosen.

Figure 16:
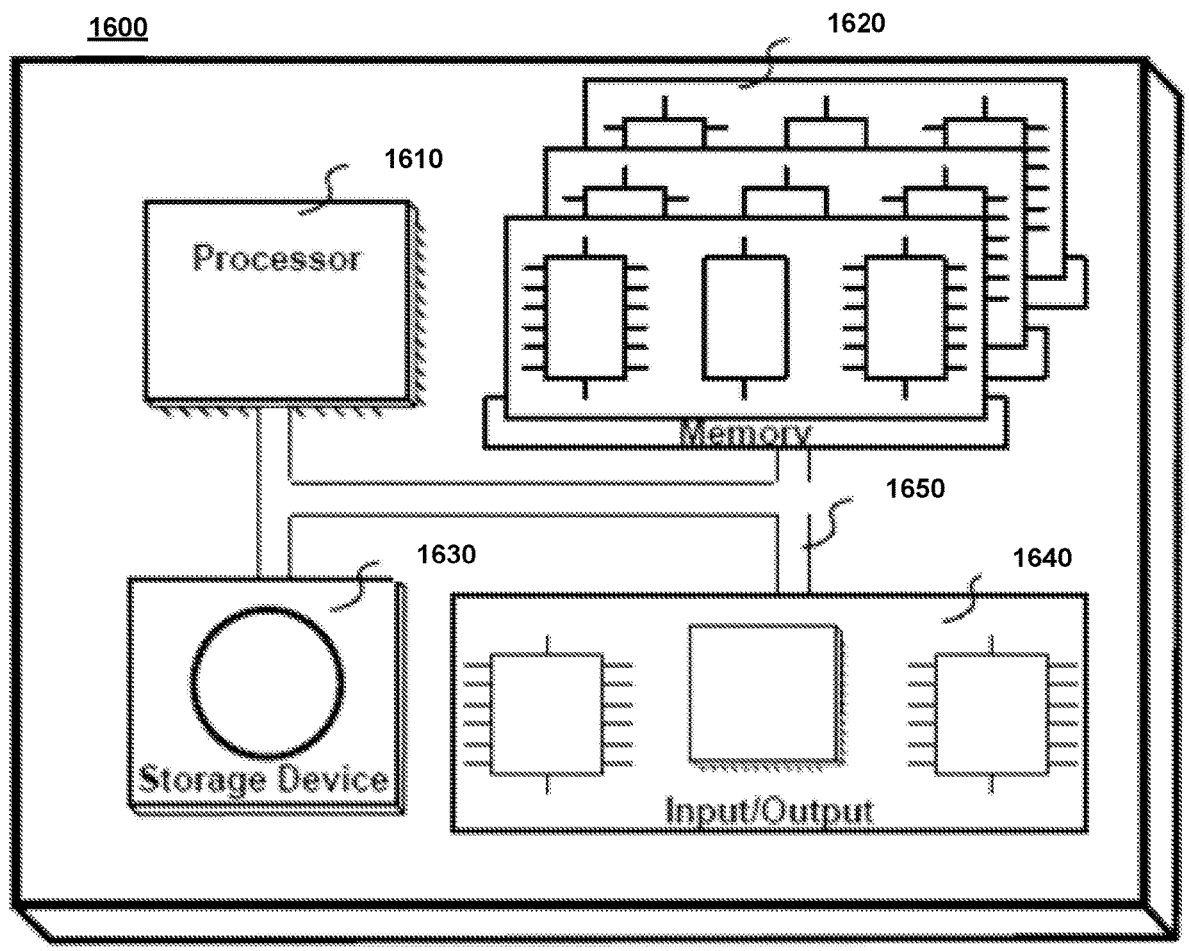
FIG. 16 is a schematic block diagram of an illustrative computer system that may be employed in systems, methods, and structures according to aspects of the present disclosure.

Finally, FIG. 16 shows an illustrative computer system 1600 suitable for implementing methods and systems according to an aspect of the present disclosure. As may be immediately appreciated, such a computer system may be integrated into another system and may be implemented via discrete elements or one or more integrated components. The computer system may comprise, for example a computer running any of a number of operating systems. The above-described methods of the present disclosure may be implemented on the computer system 1600 as stored program control instructions.

Computer system 1600 includes processor 1610, memory 1620, storage device 1630, and input/output structure 1640. One or more input/output devices may include a display. One or more busses 1650 typically interconnect the components, 1610, 1620, 1630, and 1640. Processor 1610 may be a single or multi core. Additionally, the system may include accelerators etc. further comprising the system on a chip.

Processor 1610 executes instructions in which embodiments of the present disclosure may comprise steps described in one or more of the Drawing figures. Such instructions may be stored in memory 1620 or storage device 1630. Data and/or information may be received and output using one or more input/output devices.

Memory 1620 may store data and may be a computer-readable medium, such as volatile or non-volatile memory. Storage device 1630 may provide storage for system 1600 including for example, the previously described methods. In various aspects, storage device 1630 may be a flash memory device, a disk drive, an optical disk device, or a tape device employing magnetic, optical, or other recording technologies.

Input/output structures 1640 may provide input/output operations for system 1600.

Figure 17:
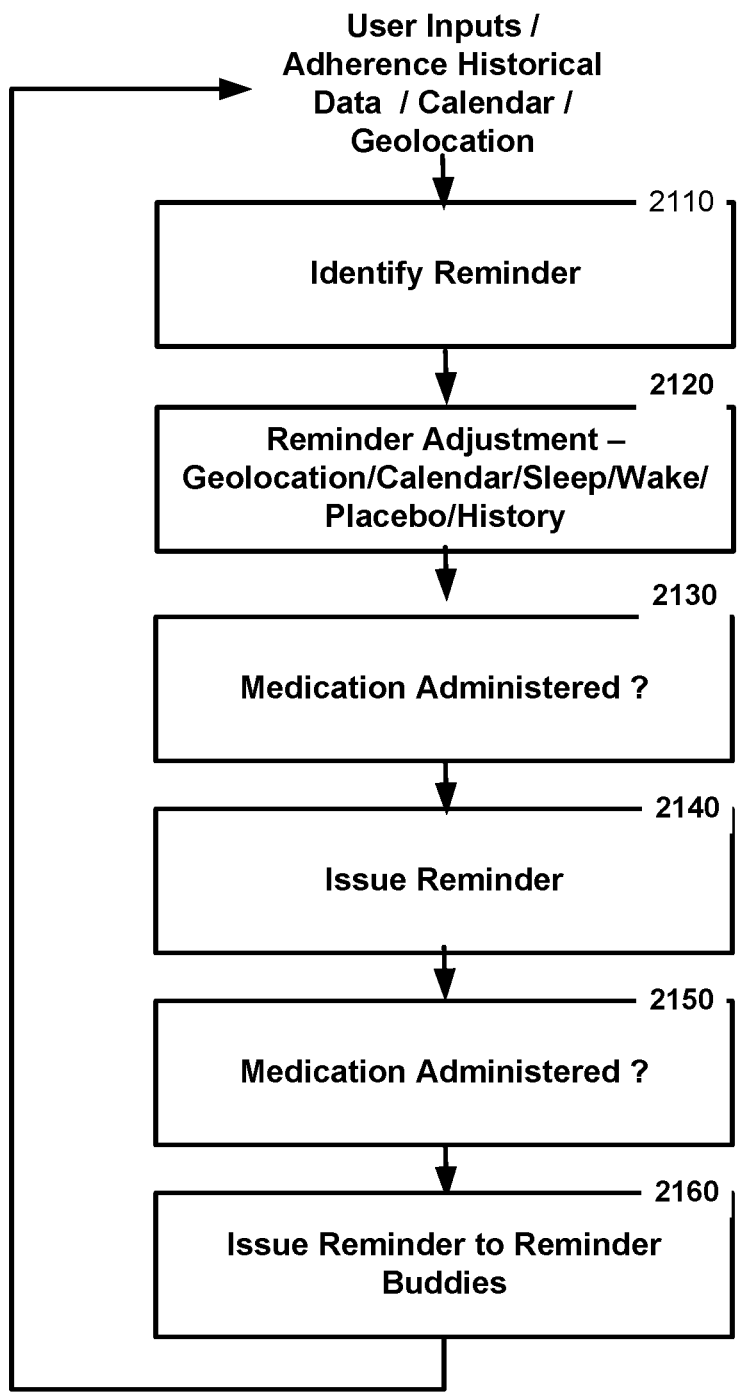
FIG. 17 is an illustrative flow diagram showing illustrative overall steps of adherence and reminder adjustment for systems, methods, and structures according to aspects of the present disclosure.

FIG. 17 is a flow diagram of an overall, high-level set of processes that determine reminder(s) and reminder adjustment based on adherence historical data/patient calendar/patient—medication location(s)/sleep/wake cycle(s)/placebo, etc. As may be observed from that figure, and as previously described—onboarding data collection/interrogation of the patient provides a substantial amount of data necessary for the reminding processes. Once a reminder is identified—Block 2110—a reminder adjustment at Block 2120—may be made based on a variety of factors including, Geolocation of the patient relative to the medicine, calendar of appointments/vacations/travel/etc. of the patient, Sleep/Wake cycle of the patient, whether a placebo is being "administered", and the adherence history(ies) of the patient and how diligently the patient has been adherent historically.

At Block 2130, a determination is made about whether or not the patient actually administered the medication—either from a smart pill container—or manually entered via APP, and if the administration did not take place, then at Block 2140 a reminder is issued to the patient. If the medication was still not administered, as determined at Block 2150, then a reminder may be issued to reminder buddies at Block 2160—still in consideration of other factors such as whether or not the buddy is in a sleep/wake cycle. This overall procedure will continue until/unless the parameters are changed and/or the overall medication regime is changed.

At this point, while we have presented this disclosure using some specific examples, those skilled in the art will recognize that our teachings are not so limited. Accordingly, this disclosure should be only limited by the scope of the claims attached hereto.

The invention claimed is:

1. A method comprising:
   receiving information associated with a patient, the information comprising an identification of a medication and a reminder time for administering the medication
   determining, by a pill case containing the medication and comprising a wireless receiver and sensing hardware, a location of the pill case, the determining based on one or more signals received by the wireless receiver;
   receiving a location of a wireless device associated with the patient;
   estimating a travel time between the patient and the pill case based on the location of the pill case and the location of the wireless device associated with the patient;
   adjusting the reminder time based on the travel time;
   providing to the patient, at the adjusted reminder time, a reminder to administer the medication;
   determining, using the sensing hardware of the pill case, whether the patient administered the medication; and
   issuing a notification if the patient does not administer the medication within a specified time interval following the reminder.

2. The method of claim 1 further comprising:
   providing FDA label-insert information for the medication to the patient.

3. The method of claim 1, wherein the information associated with the patient further comprises placebo data, and wherein the method further comprises:
   determining, based on the placebo data, that a placebo is scheduled for administration; and
   refraining from providing a reminder to administer the placebo.

4. The method of claim 3 further comprising:
   refraining from issuing a notification when the patient does not administer the placebo.

5. The method of claim 1, wherein the information associated with the patient further comprises (1) reminder text for the reminder and (2) placebo data, and wherein the method further comprises:
   setting the reminder text based on the placebo data.

6. The method of claim 1, wherein the information associated with the patient further comprises reminder text for the reminder, and wherein the reminder text is based on an adherence history.

7. The method of claim 1 wherein the wireless device associated with the patient is a smart phone.

8. The method of claim 1 further comprising:
determining, based on a calendar associated with the patient, that the patient has an insufficient supply of the medication; and
issuing a notification indicating that the supply is insufficient.

9. The method of claim 1, wherein the information associated with the patient further comprises sleep data, and wherein the adjusting of the reminder time is further based on the sleep data.

10. The method of claim 1, wherein the information associated with the patient further comprises a reminder frequency, and wherein the reminder frequency is based on an adherence history.

11. The method of claim 1 wherein the notification is provided to at least one of the patient, a reminder buddy associated with the patient, or a patient adherence advocate.

12. The method of claim 11 wherein the patient adherence advocate is one of a healthcare provider, a pharmacy, a patient affiliate, or a payer.

13. A method comprising:
receiving information associated with a patient, the information comprising an identification of a medication and a specified time for administering the medication;
determining, by a pill case containing the medication and comprising a wireless receiver, a location of the pill case, the determining based on one or more signals received by the wireless receiver;
receiving a location of a wireless device associated with the patient;
estimating a travel time between the patient and the pill case based on the location of the pill case and the location of the wireless device associated with the patient;
determining, based on the travel time, that the patient will be unable to administer the medication at the specified time; and
issuing a notification indicating that the patient will be unable to administer the medication at the specified time.

14. The method of claim 13 wherein the determining that the patient will be unable to administer the medication at the specified time is further based on
a calendar associated with the patient.

15. The method of claim 14 wherein the calendar comprises an event, a time associated with the event, and a location associated with the event.

16. The method of claim 13, further comprising:
determining a level of medication regimen adherence for the patient; and
providing the level of medication regimen adherence to one or more patent adherence advocates.

17. The method of claim 16 wherein the patient adherence advocates include at least one of a healthcare provider, a pharmacy, a patient affiliate, or a payer.

18. The method of claim 16 wherein at least one of the patent adherence advocates issues an adherence incentive that is based on the level of medication regimen adherence.

19. The method of claim 13 further comprising:
determining, based on a calendar associated with the patient, that the patient has an insufficient supply of the medication; and
issuing a notification indicating that the supply is insufficient.

20. The method of claim 13 wherein the notification is provided to at least one of the patient, a reminder buddy associated with the patient, or a patient adherence advocate.

* * * * *